United States Patent [19]

Parker et al.

[11] 4,344,768
[45] Aug. 17, 1982

[54] AUTOMATIC PIPETTOR

[75] Inventors: Bernard Parker, Westport, Conn.; Brian Parsonnet, Mamaroneck, N.Y.

[73] Assignee: Baker Instruments Corp., Bethlehem, Pa.

[21] Appl. No.: 248,531

[22] Filed: Mar. 27, 1981

[51] Int. Cl.³ .................. G01N 1/14; G01N 35/06; G01N 33/48
[52] U.S. Cl. .................. 23/230 R; 422/64; 422/72; 422/100; 73/864.81
[58] Field of Search .................. 422/64, 72, 100; 23/230 R; 73/864.81; 141/130

[56] References Cited

U.S. PATENT DOCUMENTS 3,801,283  4/1977  Shapiro et al. .................. 23/253
4,046,511  9/1977  Stabile .................. 23/259
4,235,840  11/1980  Mendoza et al. .................. 422/100 X Primary Examiner—Ronald E. Serwin
Attorney, Agent, or Firm—George W. Rauchfuss, Jr.

[57] ABSTRACT

Pipettor apparatus for automatically and rapidly transferring accurate and precise multiple quantities of samples (e.g., blood serum) and reagent to the rotatable transfer disc of a centrifugal analyzer.

25 Claims, 21 Drawing Figures

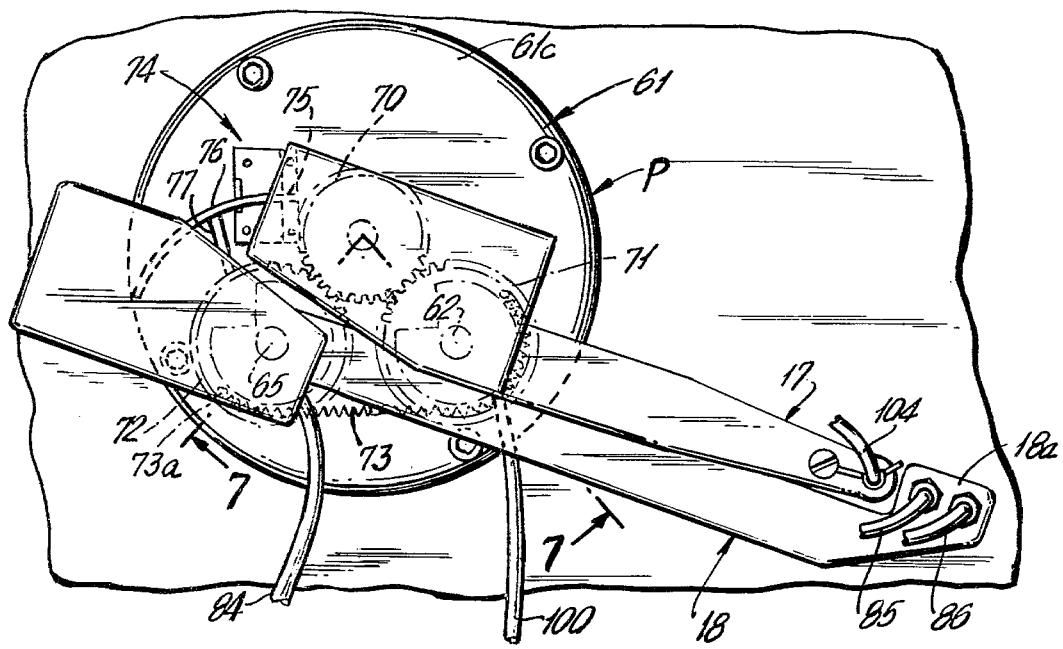
FIG. 6
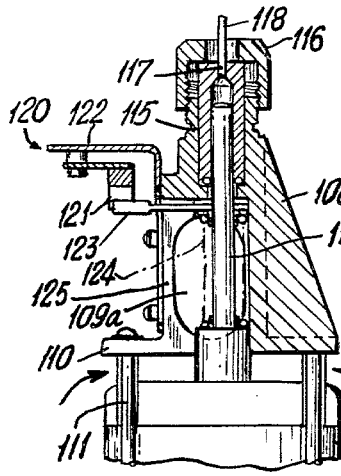
FIG. 11A
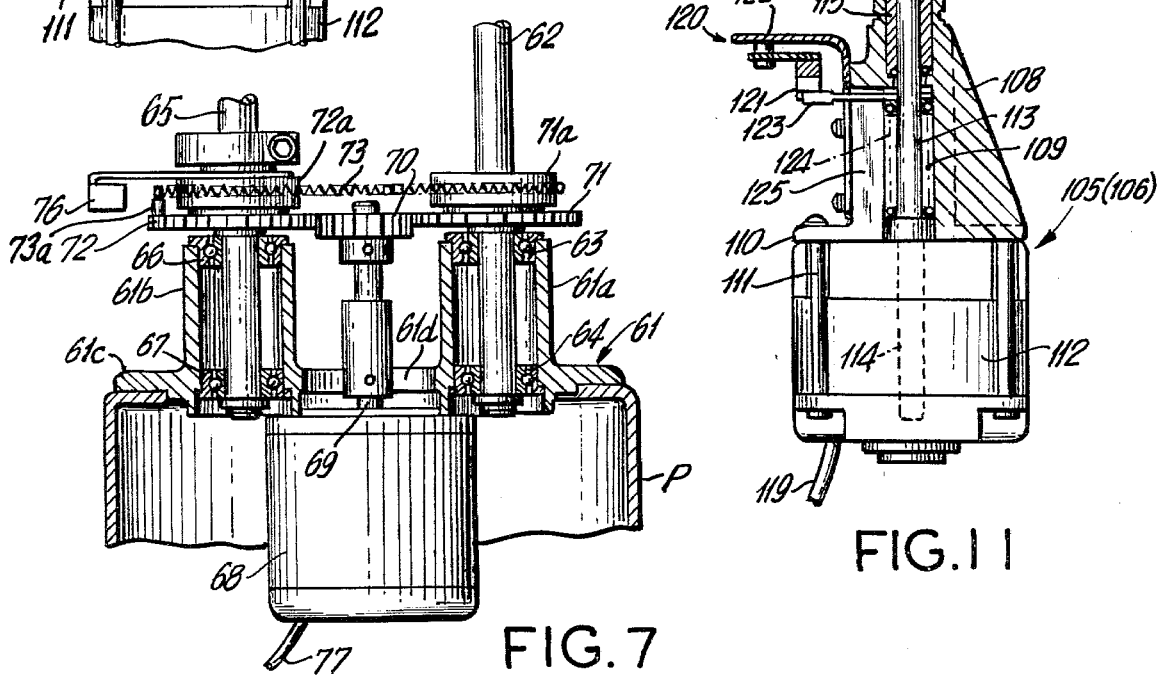
FIG. 7
FIG. 11

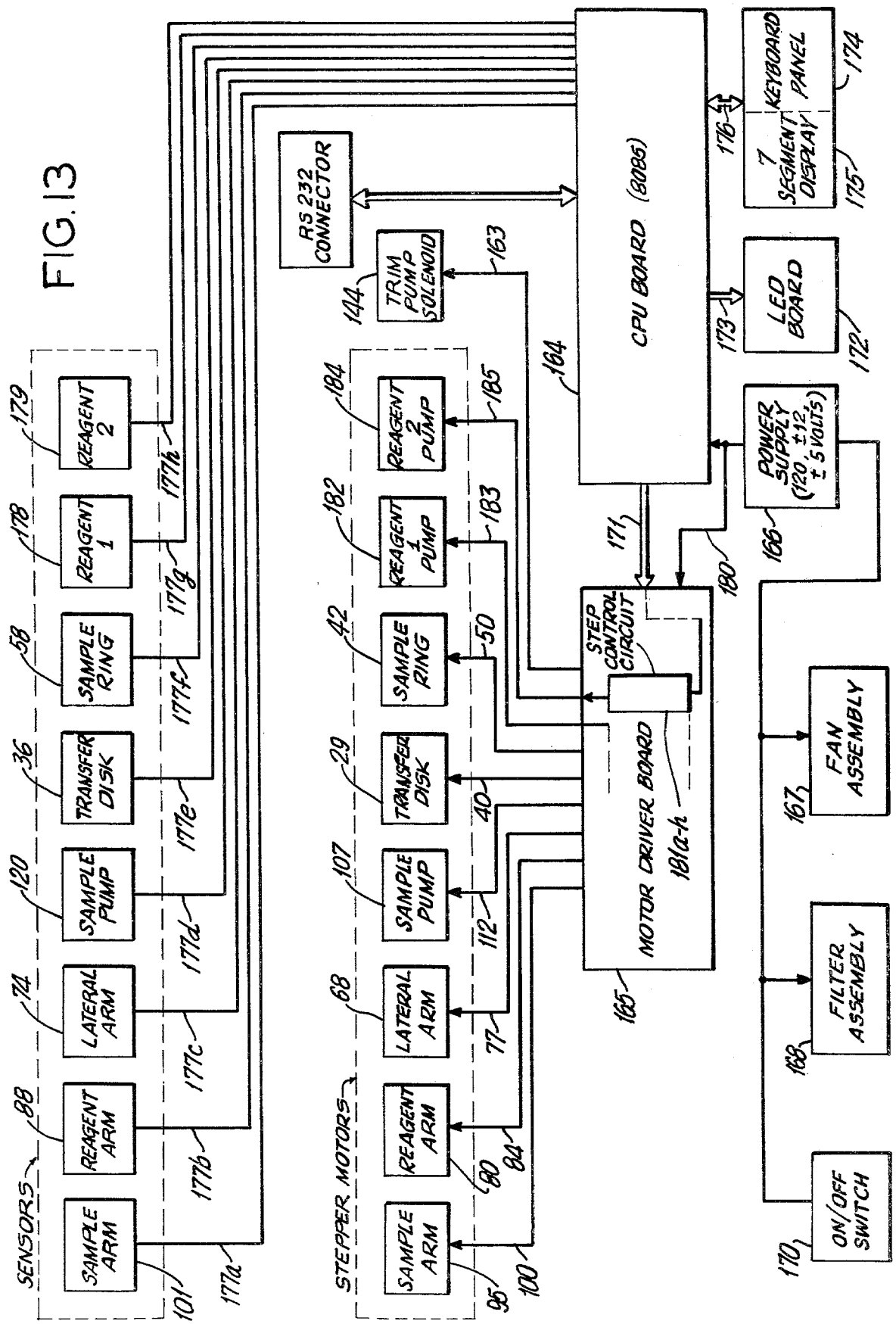

AUTOMATIC PIPETTOR

BACKGROUND OF THE INVENTION

The present invention relates to a pipettor apparatus for automatically and rapidly transferring accurate and precise multiple quantities of samples (e.g., blood serum) and reagent to the rotatable transfer disc of a centrifugal analyzer of the type disclosed in "Analytical Biochemistry", Vol. 28, pages 545-562 (1969).

More particularly, the present invention relates to a pipettor apparatus of the type described which is an improvement over the apparatus disclosed in U.S. Pat. No. 4,046,511 issued to J. Stabile on Sept. 6, 1977 and U.S. Pat. No. 3,801,283 issued to S. I. Shapiro and T. Picunko on Apr. 2, 1974.

The centrifugal analyzer of the type disclosed in the "Analytical Biochemistry" article, the disclosure of which is incorporated herein by reference, utilizes a centrifugal field to transfer sample and reagents from a series of radially aligned cavities in a rotatable transfer disc to an analyzing device. More specifically, the system is basically a series of cuvets arranged around the periphery of a rotor so that when it is spun together with the transfer disc, centrifugal force simultaneously mixes and transfers reagents and samples to the cuvets where an analysis is made spectrophotometrically.

In operation, the rotatable transfer disc is first filled with samples and reagents by suitable means such as an automatic pipettor apparatus disclosed in the above-mentioned U.S. patents. The transfer disc contains rows of cavities arranged radially therein with each cavity having an inner and outer section for reagent and sample, respectively. Each sample to be analyzed is placed individually in the outer section of a cavity and the reagent is placed in the inner section of the same cavity. The transfer disc is then taken from the pipettor and placed on a rotor in the analyzer where it is suitably indexed. As the rotor and transfer disc are accelerated, centrifugal force propels the sample and the reagent through communicating passageways to the individual cuvets within the rotor where they are mixed. The filled cuvets rapidly spin between a light source and photometric detector and the transmission of light through the cuvets, i.e., through the reacting solution, is then measured.

It is important in utilizing analyzers of the type described that the sample and reagent be introduced to the transfer disc rapidly and in accurate amounts in order to ensure accuracy of the test, to avoid wastage of expensive reagents and to reduce the time required and hence the expense of testing.

Pipettor apparatus of the type disclosed in the above-noted U.S. patents have heretofore performed satisfactorily in operation of the analyzer system but they are nonetheless subject to certain limitations. For example, the operation of these pipettor apparatus is based upon a complicated mechanical cam arrangement which is not flexible enough to permit many variations in the pipetting procedure.

It is, therefore, an object of the present invention to provide an improved pipettor apparatus for automatically and rapidly transferring accurate multiple quantities of sample and reagent to the rotatable transfer disc of a centrifugal analyzer.

A more specific object of the present invention is to provide such an improved pipettor apparatus which is far more flexible in operation when compared to similar pipettors of the prior art and which is capable of performing a number of pipetting procedures which were not possible heretofore.

DESCRIPTION OF THE DRAWING

FIG. 6 is an enlarged top plan view of the reagent transfer arm and the sample transfer arm and showing the lateral drive mechanism therefor in phantom lines.

FIG. 7 is an elevational, sectional view taken along the lines 7—7 in FIG. 6 showing the drive mechanism for operating both transfer arms.

FIG. 11 is an enlarged elevational, sectional view taken along the line 11—11 in FIG. 4 showing one of the delivery pumps used for dispensing sample solution.

FIG. 11A is a similar view taken along the line 11A—11A in FIG. 4 showing another delivery pump used for dispensing reagent solution.

FIG. 13 is a block diagram showing an arrangement of electrical circuit components used for operating the pipettor apparatus of the present invention.

DESCRIPTION OF A PREFERRED EMBODIMENT

Figure 1:
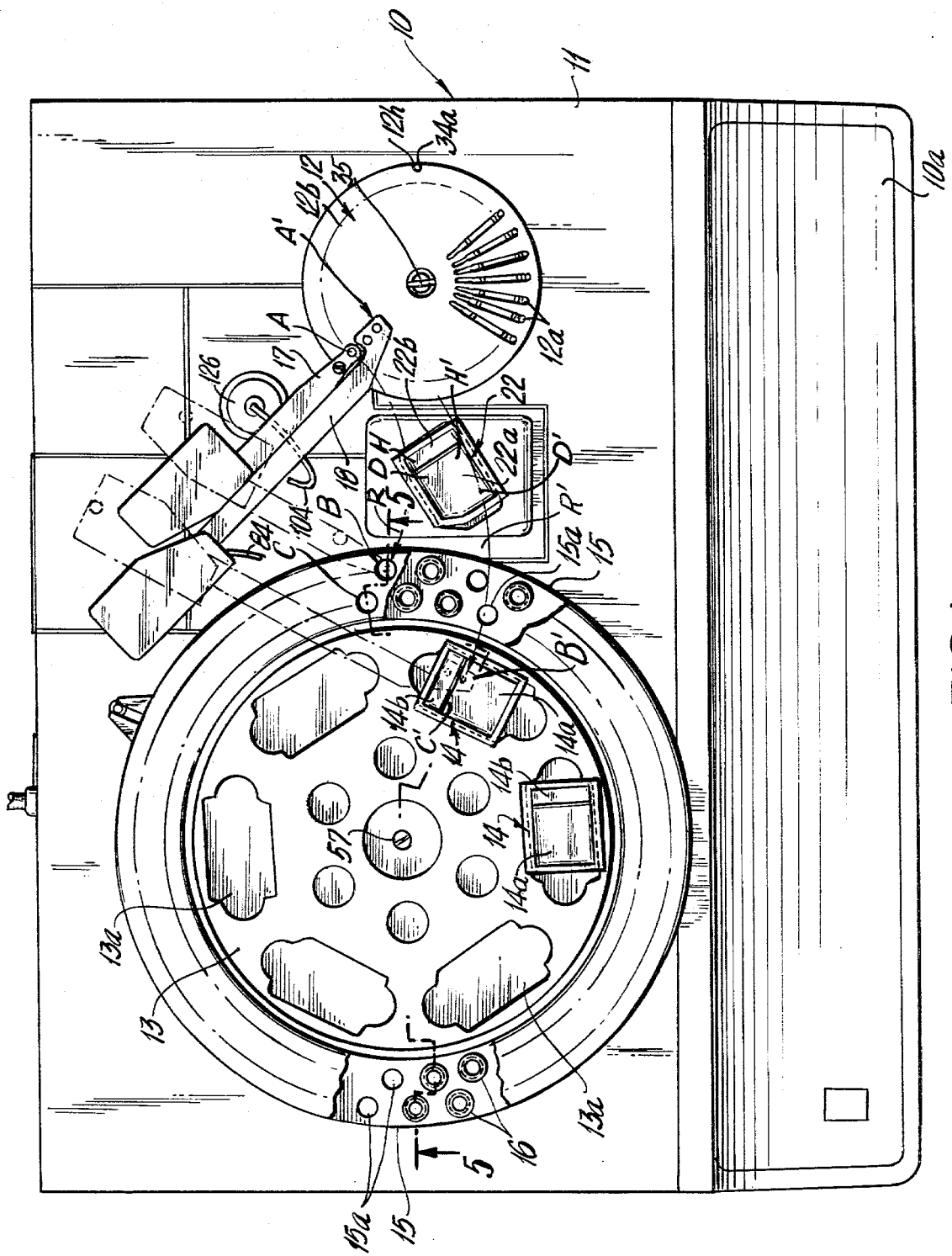
FIG. 1 is a plan view of an automatic pipettor apparatus in accordance with the present invention showing the general arrangement of elements involved in the loading of a multicavity transfer disc with reagent and samples.

With reference to the drawing, and particularly FIGS. 1-5 inclusive, there is shown an improved pipettor apparatus in accordance with the present invention. As shown, the pipettor apparatus includes a rectangular, metallic case 10 having an oblique front panel 10a and a removably, molded plastic top cover 11. The case 10 is made from cast aluminum, for example, and the top cover 11 is preferably molded from a high strength, plastic material such as Cycolac (Trademark of Borg Warner). All of the operating elements of the pipettor are mounted over the top cover 11 in a manner to be hereinafter described and are fully accessible to the operator at all times. These elements include, for example, a removable transfer disc 12 having a multiplicity of elongated radial cavities 12a into which the sample and reagent are automatically and individually dispensed, a circular reagent tray 13 having a number of circumferentially disposed oblong pockets as at 13a for holding an equal number of reagent containers 14 (there being six such pockets in the embodiment of the apparatus shown and only two reagent containers illustrated for purposes of simplicity), a removable sample ring 15 mounted around the outer circumference of the circular reagent tray 13 and including a multiplicity of small holes 15a arranged in two separate circumferential rows for holding a multiplicity of small sample vials 16 (see FIG. 5) and a pair of vertically and laterally movable transfer arms 17 and 18. One of the transfer arms 17 has mounted at its outer end a pipettor nozzle 19 (see FIGS. 9 and 10) for picking up specified quantities of sample specimen from each sample vial 16 and transferring this sample specimen to one of the cavities 12a in the transfer disc 12. The other transfer arm 18 has mounted at its outer end a pair of similar pipettor nozzles 20, 21 (see FIG. 8) for picking up at least one reagent solution from a reagent container 14 and transferring this reagent solution to the same cavity 12a in transfer disc 12. The reagent container 14 has two compartments 14a, 14b for holding two separate reagent solutions, if desired. Also mounted on the top cover 11 between the transfer disc 12 and sample ring 15 is a removable wash container 22 having two compartments 22a, 22b, one of which compartments 22a holds fresh diluent for cleaning the pipettor nozzles in a manner to be hereafter described and the other of which compartments 22b holds spent or contaminated diluent. The procedure for transferring both sample specimen and reagent to the individual cavities 12a in transfer disc 12 is carried out in a series of steps in which both the transfer disc and sample ring 15 are rotated or indexed to a specific location depending on the sample and the test, etc. The transfer arms 17, 18 are also moved in both a vertical and lateral direction in order to pick up and transfer sample specimen and reagent and also to perform certain cleaning procedures as shall be described hereinafter. It should be noted at this point that the drive mechanism for the transfer arms 17, 18 is designed such that the arms are free to move independently only in the vertical direction. It should also be noted that when the arms are moved to an extreme end of their travel over the transfer disc 12, the two transfer arms 17, 18 are parallel and juxtaposed to one another with the shorter sample arm 17 located behind an outward extension 18a formed at the outer end of reagent arm 18. This arrangement of the two arms 17, 18 enables the sample nozzle 19 (FIG. 9) and the two reagent nozzles 20, 21 (FIG. 8) to be maintained in alignment with one another when disposed radially over one of the cavities 12a in the transfer disc 12, these positions of the sample and reagent nozzles being hereinafter referred to as the "dispense" positions A and A', respectively. It will be further seen that when moved to the opposite extreme end of their travel, the two transfer arms 17, 18 are spaced apart in parallel relationship to one another as illustrated in phantom lines in FIG. 1, the shorter sample arm 17 being placed with the sample nozzle 19 located over one of the vials 16 and the longer reagent arm 18 being placed with each of its two reagent nozzles 20, 21 located over each of the two compartments 14a, 14b in the reagent container 14. It will, of course, be understood that the apparatus may be operated with one or two reagents depending upon the particular test to be conducted. If the only one reagent is to be used, then this reagent is placed in one of the compartments 14a while the remaining compartment 14b is left empty.

Figure 2:
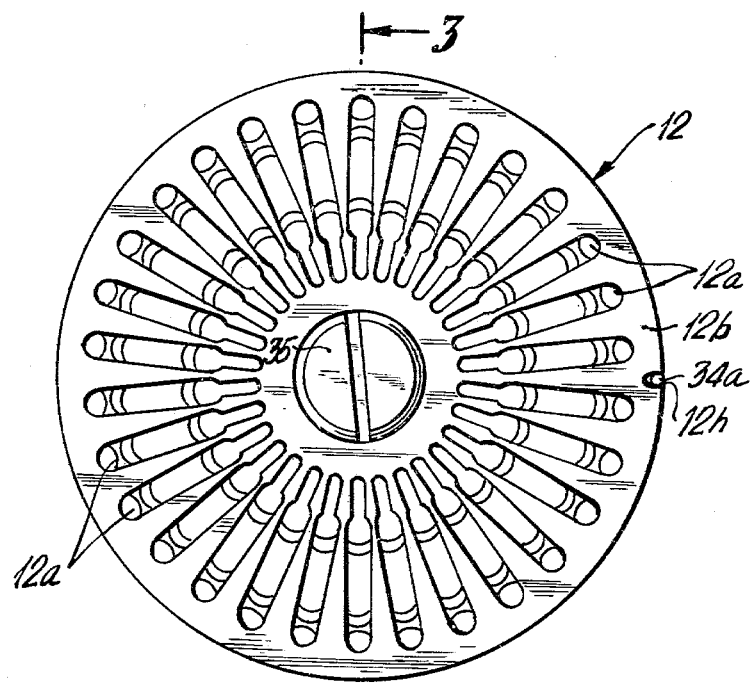
FIG. 2 is an enlarged plan view of the multicavity transfer disc shown in FIG. 1.
Figure 3:
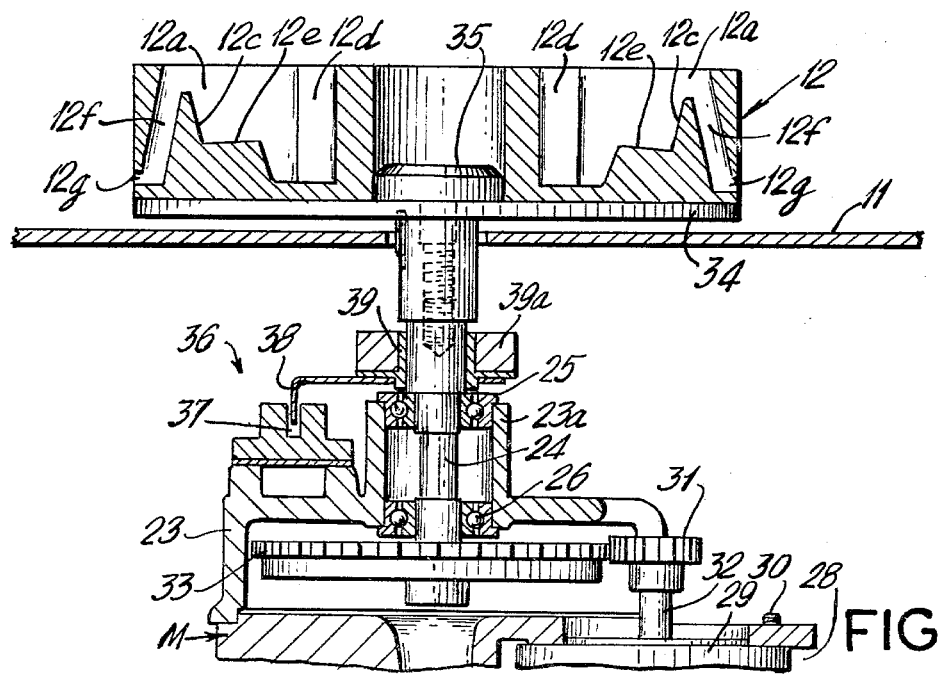
FIG. 3 is an enlarged elevational, sectional view taken along the lines 3—3 in FIG. 1 showing the multicavity transfer disc and the drive mechanism therefor.

The removable transfer disc 12 is shown in greater detail in FIGS. 2 and 3. The disc is molded in one piece from a suitable plastic material such as Teflon, for example, and has the plurality of radial cavities 12a formed within its top surface 12b. Each cavity 12a comprises two sections separated by an inclined wall 12c, i.e., an inner reagent section 12d and an outer sample section 12e. Operating procedure involves the placing of the sample and reagent in the respective sections of each cavity and then loading the transfer disc 12 into the analyzer where the disc is spun. Centrifugal force moves the contents of the sample and reagents to an outer passageway 12f where they are mixed and transferred through channels 12g to the individual cuvets (not shown) for analysis. In the embodiment of the transfer disc shown, there are a total of thirty cavities into which sample and reagent solution are automatically and individually dispensed.

Figure 4:
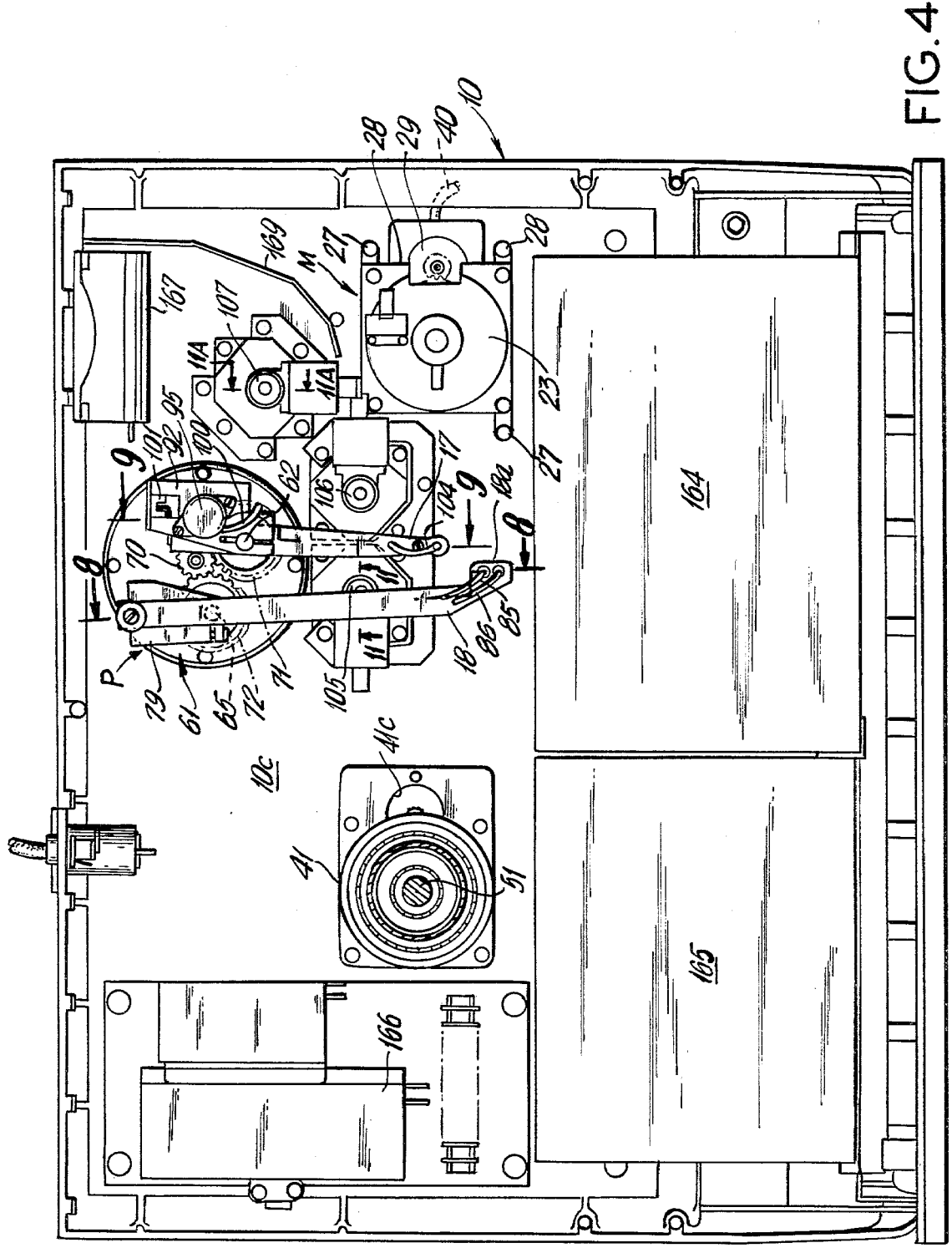
FIG. 4 is a top plan view of the pipettor apparatus of the present invention similar to FIG. 1 but with the top cover removed and showing both the mechanical and electrical elements used in the operation of the apparatus.

As further shown in FIGS. 3 and 4, the drive mechanism for rotating the transfer disc 12 includes a bell shaped, metallic housing 23 which is formed with a central tubular stem 23a for mounting a drive shaft 24. The drive shaft 24 is axially mounted in the tubular stem 23a by a pair of ball bearings 25, 26. The housing 23 is mounted on top of a rectangular, metallic stand-off M which is in turn bolted to the bottom wall 10c of the case 10 as shown at 27 (see FIG. 4). The stand-off M is formed with an open end section 28 which accommodates an electric stepper motor 29. The stepper motor 29 is mounted vertically inside the stand-off M via bolts 30 and has a pinion gear 31 secured to the end of the motor drive shaft 32. The pinion gear 31 engages a larger diameter gear 33 secured to the lower end of the drive shaft 24 inside the housing 23. The transfer disc 12 is removably mounted on top of a circular support plate 34 which is in turn secured to the upper end of the drive shaft 24 by a shoulder screw 35.

The drive mechanism for rotating the transfer disc 12 also includes an optical homing device as generally indicated at 36. This device is of a conventional design including a light source and a photo sensitive element (not shown) separated by a space 37. A sensor arm 38 is attached to sleeve 39 mounted on the shaft 24 via clamp 39a. The arm 38 enters space 37 and intercepts the beam of light passing between the light source and the photo sensitive element.

The transfer disc 12 is placed on top of the support plate 34 with the appropriate cavity for cuvet "O" located at the home position. This is accomplished by provision of a locating pin 34a on the periphery of the support plate 34 which engages a slot 12h on the transfer disc.

Although not shown in detail in the drawing, the stepper motor 29 is also of a conventional design and includes a plurality of oppositely polarized, stationary magnetic poles circumferentially arranged around a rotor which engages the drive shaft. The motor is activated by a series of electrical pulses fed through cable 40 (FIG. 4) which sequentially energize the pairs of stationary magnetic poles and the rotor will turn through predetermined angular displacements with each pulse. Typically, in the embodiment of the pipettor apparatus shown, forty electrical pulses will rotate the stepper motor through a total displacement of 60°. The gear ratio between the pinion and large diameter gears is chosen (5:1) such that this number of electrical pulses will in turn rotate the transfer disc 12 through a predetermined angular displacement of about 12° which individually indexes each of the cavities 12a to the "dispense" positions A and A'.

Figure 5:
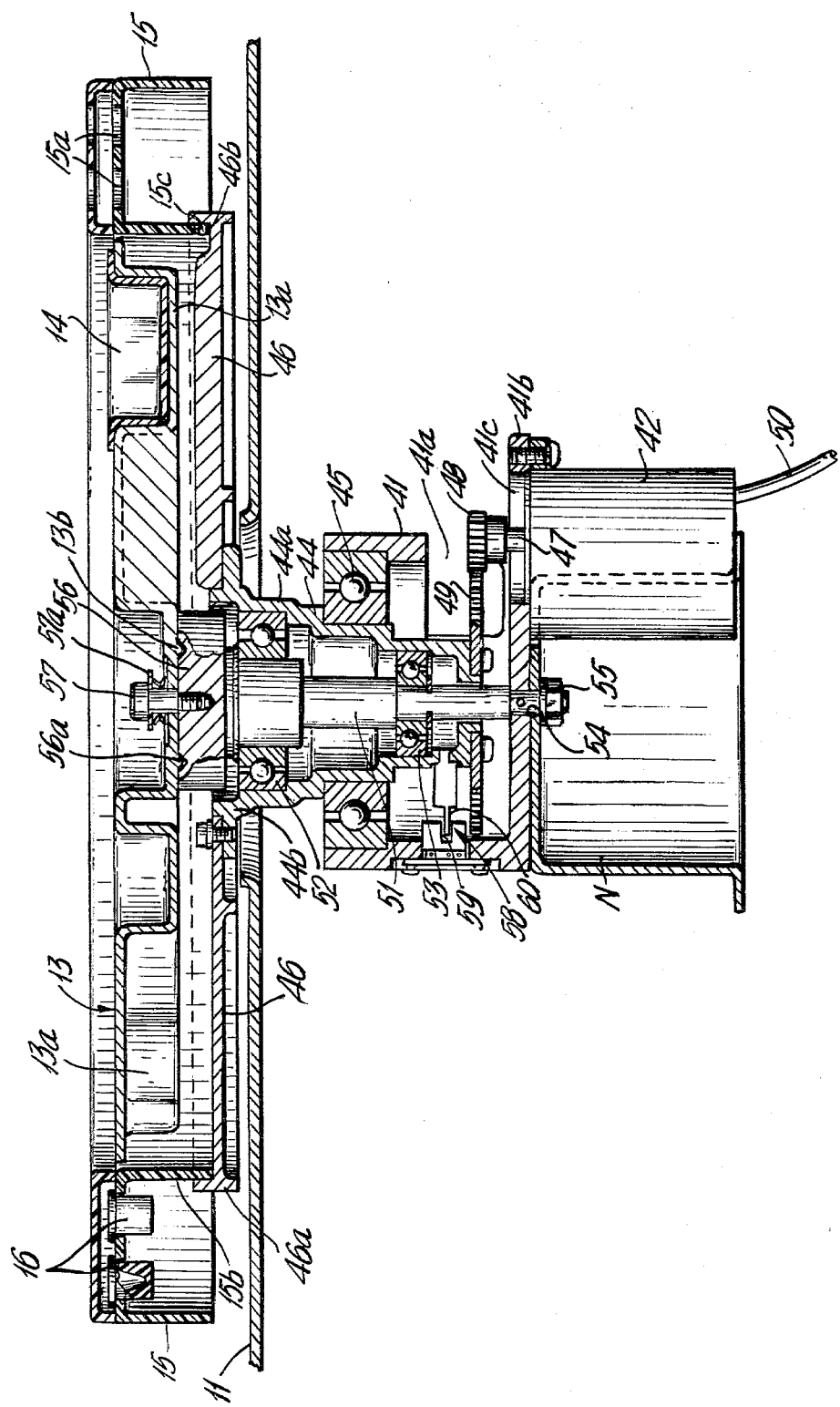
FIG. 5 is an elevational, sectional view taken along the lines 5—5 in FIG. 1 showing the reagent tray and the sample ring and drive mechanism therefor.

The reagent tray 13 and sample ring 15 are more particularly shown in FIG. 5 along with the associated drive mechanism for rotating the sample ring. The reagent tray 13 is molded in one piece from a suitable plastic material, eg Cycolac, together with the desired number of pockets 13a for holding the individual reagent containers 14, e.g., six in the embodiment of the apparatus shown. Each reagent container 14 holds one or two reagents, as the case may be, that are necessary to carry out a single test; hence, six tests can be carried out with this particular apparatus without changing the reagent container.

Similarly, the sample ring 15 is molded in one piece from a suitable plastic material, e.g., Cycolac, and has a generally U-shaped section as shown. The ring 15 is also molded together with the desired number of holes 15a for holding the individual sample vials 16. In the embodiment of the apparatus shown, there are two rows of holes for holding a total of ninety-six vials.

The drive mechanism for the sample ring 15 includes a generally cupped shaped metallic housing 41 having a cut-out section in one portion of its side wall as at 41a along with an extended bottom wall 41. The bottom wall 41b has a large opening 41c to accommodate another electric stepper motor 42. The housing 41 is similarly mounted on top of a rectangular hollow stand-off N which is also secured to the bottom wall 10c by bolts (not shown).

An outer tubular, telescopic shaped drive shaft 44 is mounted inside the metallic housing 41 by means of the ball bearings 45. The shaft 44 has removably affixed thereto an annular support disc 46 at its upper larger diameter end 44a which is also formed with an annular mounting flange 44b for this purpose. The disc 46 is secured to the annular flange 44b by set screws and has at its outer edge a peripheral rim 46a. The sample ring 15 is removably mounted onto the disc 46 by simply placing its innermost wall 15b inside the peripheral rim 46a. In order to insure alignment of the sample ring 15 on the support disc 46, detent 46b is formed just inside the rim 46a and engages a slot 15c formed in the sample ring wall 15b.

The stepper motor 42 is mounted to the underneath side of the bottom wall 41b with its drive shaft 47 extending through the large opening 41c into the cut-away section 41a and is secured by set screws or the like. A pinion gear 48 is mounted to the end of the shaft and engages a larger diameter gear 49 which is secured to the lower smaller diameter end of the tubular drive shaft 44. The gear ratio between the pinion gear 48 and the gear 49 is chosen such that when the stepper motor 42 is activated by a given number of electrical pulses fed through cable 50, the sample ring 15 will rotate through a predetermined angular displacement which indexes one of the vials 16 containing a specific sample at the "sample pick-up" position at "B" for the outer row of sample vials and at "C" for the inner row in FIG. 1.

Another telescopic, smaller diameter shaft 51 is mounted inside the tubular drive shaft 44 by the pair of ball bearing 52, 53 and has its lower, smaller diameter end fixedly secured within an aperture 54 in bottom wall 41b by means of nut 55. The uppermost end of the shaft 51 is formed with a circular disc 56 on which the reagent tray 13 is fixed by a shoulder screw 57. It will be seen then that the reagent tray 13 and the shaft 51 are coaxially mounted within the sample ring 15 and its associated drive mechanism and further that the tray 13 can be rotated independently by hand in order to locate any one of the reagent containers 14 at the "reagent pick-up" positions designated at B' and C', respectively, in FIG. 1.

As shown in FIG. 5, there is also provided an arrangement for locking the sample tray 13 in place which includes a locating detent 13b provided in the bottom wall of the tray and adapted to engage any one of a number of small V-slots 56a formed at spaced intervals in a circumferential row within the top surface of the disc 56. In the embodiment of the pipettor shown, there are six such slots 56a one for each of the six reagent containers 14 held in the tray. A spring 57a is placed beneath the shoulder screw 57 and biases the bottom wall of the tray including detent 13b against the disc 56. Thus, when it is desired to rotate the tray 13 and index a given reagent container 14 at the pickup position, the tray is rotated by hand overcoming the pressure exerted by spring 57a until the detent 13b re-engages the appropriate V-slot 56a.

The drive mechanism for the sample ring 15 is provided with an optical homing device as generally indicated at 58. This device includes a light source and a photosensitive element (not shown) separated by a space 59. A sensor arm 60 is attached to the lower end of the tubular drive shaft 44 and moves through the space 59 and interrupts the light beam.

FIGS. 6 and 7 show in greater detail the drive mechanism for rotating both of the transfer arms 17, 18 in the lateral direction. This mechanism includes a metallic housing 61 having a pair of vertical, cylindrical sections 61a, 61b which are both formed integrally with a circular base section 61c. A drive shaft 62 for rotating the sample arm 17 is mounted within one cylindrical section 61a by a pair of ball bearings 63, 64. Similarly, a drive shaft 65 for rotating the reagent arm 18 is mounted within the other vertical, cylindrical section 61b by a pair of ball bearings 66, 67. An electric stepper motor 68 is mounted to the underneath side of the circular base section 61c with its drive shaft 69 extending through a large opening 61d formed in the center of the base section. A pinion gear 70 is secured to the end of the shaft 69 and engages simultaneously each one of a pair of larger diameter gears 71, 72 secured respectively to the drive shaft 62 for the transfer arm 17 and drive shaft 65 for the transfer arm 18. An elongated coil spring 73 is wrapped around a portion of the gear hubs 71a, 72a and is anchored at each end to the gears 71, 72, respectively, such as by lugs 73a. This arrangement serves to apply a small tongue to each of the drive shaft 62, 65 which, in turn, maintains the transfer arms 17 and 18 in proper relation to one another. The metallic housing 61 is mounted on top of a hollow metallic stand-off P which is fixed to the bottom wall 10c (FIG. 4). By this arrangement, it will be seen that the two transfer arms 17, 18 are driven in unison by the pinion gear 70 and stepper motor 68. It will also be seen that the cylindrical sections 61a, 61b are located in such geometric arrangement with respect to each other that the transfer arms 17, 18 mounted on the shafts 62, 65 are placed in juxtaposition to each other including their respective pipettor nozzles 19, 20 and 21 which are held in alignment over a single cavity 12a at the "fill" positions A and A' shown in FIG. 1. At the same time the transfer arms 17, 18 are placed in spaced apart parallel relationship when they are moved to the "pick-up" positions B and C or B' and C' if the sample vial is located within the inner row as shown in phantom lines in FIG. 1.

As best shown in FIG. 6, the drive mechanism for the two transfer arms 17, 18 includes an optical homing device as generally indicated at 74. This device comprises a light source and an photo sensing element (not shown) separated by a space 75. A long, arcuate shaped interruptor arm 76 is attached to shaft 65 (see FIG. 7) and moves through the space 75 when the stepper motor is activated via cable 77 to rotate shaft 65.

In their home positions, the two transfer arms 17, 18 are located preferably at a point intermediate the transfer disc 12 and the sample ring 15 as best illustrated in FIG. 4. Thus, the interruptor arm 76 is adjusted on the shaft 65 to place the arm in space 75 where it will interrupt the light beam when the transfer arms 17, 18 are moved to this position.

Figure 8:
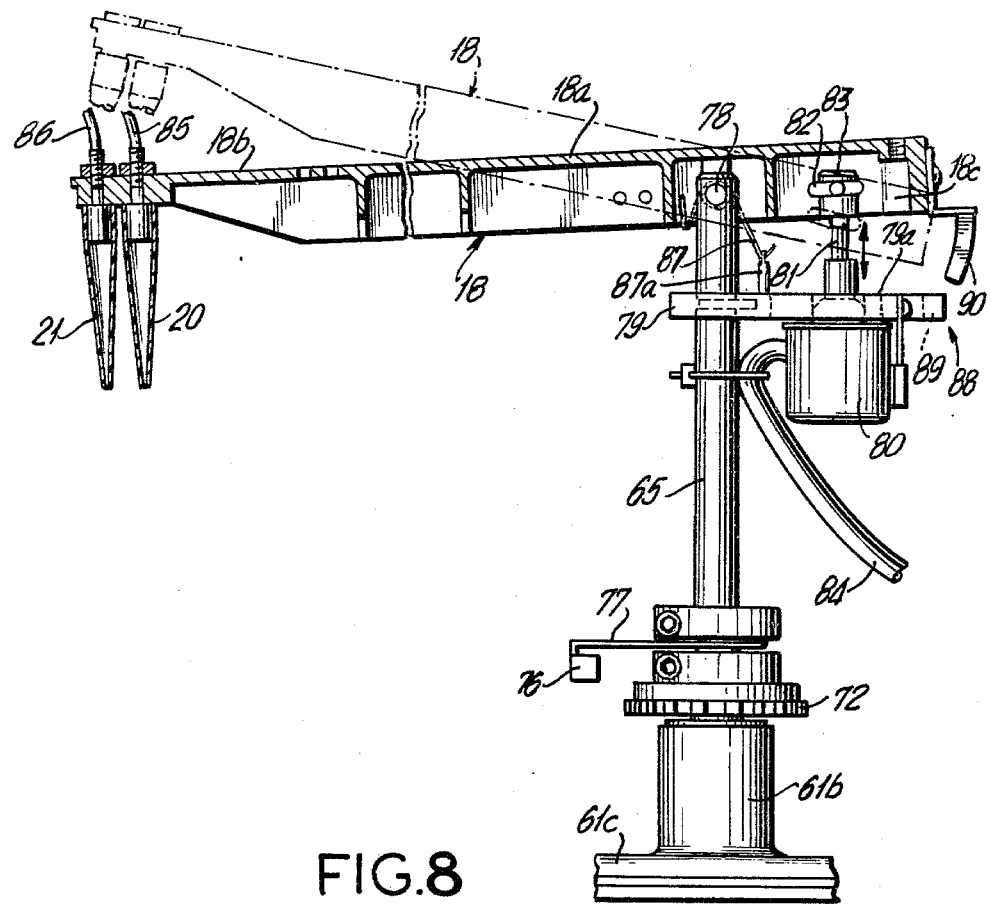
FIG. 8 is an enlarged elevational, sectional view taken along the lines 8—8 in FIG. 4 showing the reagent transfer arm and its vertical drive mechanism.

The reagent transfer arm 18 and its associated drive mechanism for moving the arm in the vertical direction are shown in greater detail in FIG. 8. The reagent transfer arm 18 is molded in one piece from a suitable plastic material such as Cycolac, for example, and has a generally U-shaped cross section (not shown) with a flat top surface 18a. The transfer arm 18 is mounted to the drive shaft 65 at a location approximately one-third the distance from the rearward end 18c by a pivot pin 78. A metallic support plate 79 is fixedly attached to the shaft 65 and has a large aperture 79a for mounting a stepper motor 80.

The stepper motor 80 is secured to the underneath side of the plate 79 with its drive shaft 81 extending through the aperture 79a into the rearward end 18c of the transfer arm 18. The two opposite side walls of the transfer arm 18 are provided with elongated slots 82 (only one slot being shown in the view of the FIG. 8) to accommodate in sliding engagement therewith a pin 83 which extends through the uppermost end of the drive shaft 81.

The stepper motor 80 in this instance is a "linear" stepper motor which is similar to the stepper motors described before except that the drive shaft is locked or keyed to prevent its rotation together with the rotor. Instead the shaft is free to move in the linear direction as the rotor is caused to rotate with each successive electrical pulse. The drive shaft 81 will move in an upward or downward direction without itself rotating depending upon the polarity and number of electrical pulses fed to the motor through the cable 84. This will in turn lower or raise the forward end 18b of the transfer arm 18 including the pair of reagent nozzles 20, 21. The nozzles 20, 21 are each provided with a flexible tube 85, 86, respectively, attached to the upper end of the nozzles for pick up of the reagent. A spring 87 is coiled around the pin 78 and is anchored at one end to a lug 87a fixed to the plate 79. The other end of the spring 87 is bend around and locked to the side wall of the arm 18. This arrangement biases the transfer arm 18 in a direction toward its raised or home position shown in phantom lines in FIG. 8.

The drive mechanism for moving the reagent arm 18 in the vertical direction is similarly provided with an optical homing device as generally inidicated at 88. This device also includes a light source and photo sensitive element (not shown) separated by a space 89. An arcuate shaped arm 90 is attached to the rearward end 18c of the transfer arm 18. It will be seen that the arm 90 will move into the space 89 and interrupt the light beam when the transfer arm 18 is raised to its home position.

Figures 9, 10:
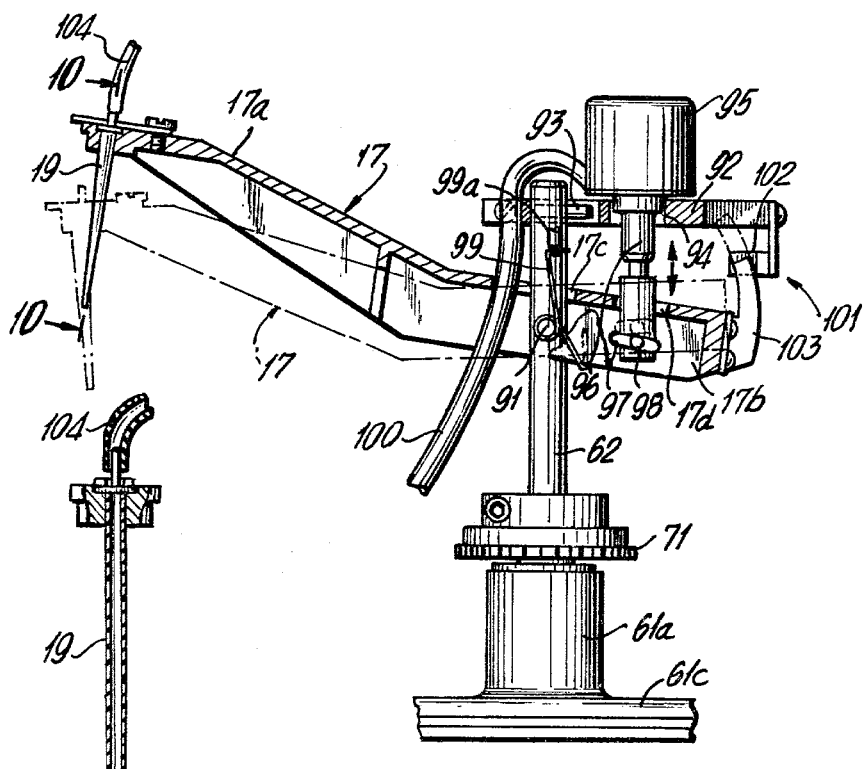
FIG. 9 is an enlarged elevational, sectional view taken along the lines 9—9 in FIG. 4 showing the sample transfer arm and its vertical drive mechanism.
FIG. 10 is an enlarged elevational, sectional view taken along the lines 10—10 in FIG. 9 showing the sample pipettor nozzle in detail.

FIG. 9 shows in detail the sample arm 17 and its associated drive mechanism for moving the sample arm in a vertical direction. The sample arm 17 is also molded in one piece from a suitable plastic material such as Cycolac, for example. The sample arm 17 is generally U-shaped in cross section and has an upwardly inclined forward end 17a and a rearward end 17b. In this instance the sample arm 17 is mounted to the drive shaft 62 at a location intermediate the upper end of the shaft and the gear 71 by a pivot pin 91. To accommodate the upper end of the shaft, the sample arm 17 is provided with an opening 17c in its top wall. A support plate 92 is aligned to the upper end of the shaft 62 by a pin 93 and has a large opening 94 for mounting another linear stepper motor 95. The motor 95 is mounted in this case to the upper side of the support plate 92 and has its drive shaft 96 extending through the opening 94 into the rearward end 17b of the transfer arm 17. The top wall of the transfer arm is similarly provided with an opening 17d to accommodate the lower portion of the shaft 96 and is also provided with elongated slots 97 in its side wall (only one such slots being shown in the view of FIG. 9) to accommodate a pin 98 which is attached to the lower end of the shaft 96. A spring 99 is coiled around the pivot pin 91 and has one end anchored by a lug 99a fixed to the underneath side of the plate 92. The other end of the spring 99 is bent around and locked to the side wall of the arm 17. This arrangement biases the sample arm 17 in a direction towards its raised or home position shown in solid lines in FIG. 9. The stepper motor 95 operates in the same manner as described above to raise or lower the forward end 17a of the sample arm 17 including the sample nozzle 19, i.e., by electrical pulses fed to the motor 95 through the cable 100.

The drive mechanism for the sample arm 17 is also provided with an optical homing device as generally indicated at 101. This device also includes a light source and a photosensitivity element (not shown) separated by a space 102. An arcuate shaped arm 103 is fixed to the rearward end 17b of the transfer arm 17. In this instance, when the sample arm 17 is moved to the home position as shown in full lines in FIG. 9, the arm 103 exits the space 102 and permits the light beam to fall on the photosensitive element.

In FIG. 10, there is shown an enlarged cross-sectional view of a typical sample nozzle 19 which is of an enlongated, needle-like configuration. A flexible tube 104 is also shown attached to the upper end of the nozzle 19 for pick up of the sample specimen as shall be described.

Three separate delivery pumps 105, 106 and 107 are provided for use in combination with the two reagent nozzles 20, 21, and the sample nozzle 19, respectively. The sample pump 107 is shown in enlarged detail in FIG. 11. As shown, the pump includes a metallic housing 108 having an axial bore 109 and a base section 110 which is secured by bolts 111 to the top of a linear stepper motor 112. An elongated, small diameter piston 113 is movably disposed inside the axial bore 109 and is attached at its lower end to the drive shaft 114 of the stepper motor 112. The piston 113 extends into a tubular sleeve 115 mounted inside the upper end of the axial bore 109 and secured in place by an annular cap 116 threaded onto the upper end of the housing 108. The sleeve 115 has a small aperture 117 at its end into which is fitted one end of a stainless steel tube 118 extending through the cap 116. The tube 118 communicates at its other end via a flexible tube (i.e., tube 104 in FIGS. 6 and 9) to the sample nozzle 19. The operation of the stepper motor 112 is basically the same as the linear stepper motors used for vertical movement of the two transfer arms 17, 18, i.e., the shaft 114 moves in response to a series of electrically pulses fed to the stepper motor 112 via the cable 119.

The sample pump 107 also includes a homing device as generally indicated at 120. This device includes a light source and a photosensitive element (not shown) which are separated by a space 121. Suitably, the homing device is supported by a bracket 122 which is secured to the sidewall of the housing 108. An elongated sensor arm 123 is mounted on the piston 133 which is surrounded by a coil spring 124 to stabilize its motion inside the bore 109. The arm 123 moves in an upward or downward direction together with the piston 113 in a slot 125 provided in the sidewall of the housing 108 and enters the space 121 to interrupt the light beam when the piston 113 reaches the full extent of its upward travel inside the sleeve 115.

The two reagent pumps 105,106 are basically the same as the sample pump 107 except that in this case provision is made for cooling the interior parts of the pump. Thus, as shown in FIG. 11A, each reagent pump includes a metallic housing 108a in which the axial bore is essentially replaced by a large vent opening 109a. In addition, the housing 108a is mounted in spaced apart relation on top of the stepper motor 112 by the bolts 111 to provide addition space for passage of coolant air as indicated by the arrows in the drawing.

The two reagent pumps 105 and 106 are used independently with each of the reagent nozzles 20, 21. However, in the embodiment of the pipettor apparatus shown, the sample pump 107 operates in conjunction with an adjustable volume delivery pump 126 which is mounted within the top cover 11 as illustrated in FIG. 1. This pump which is also referred to hereinafter as the "trim pump", is disclosed and claim in the copending application Ser. No. 221,152 of Bernard Parker filed on Dec. 29, 1980, the disclosure of which is incorporated herein by reference. As shall be made more clear hereinafter, the combined sample pump 107 and trim pump 126 are capable of dispensing accurate and precise amounts of liquid even in those instances where the quantity of liquid to be handled is very small such as less than about one drop (each drop of water, for example, equals about 20 to 30 microliters). The problem is that the liquid held inside the pipettor nozzle will usually form a convex or concave meniscus at the nozzle tip depending on several factors, e.g., surface tension of the liquid, the speed of delivery etc. The difference in volumetric displacement that occurs in the case of two nozzles otherwise identical except that they each contain a liquid forming a different meniscus at the tip can result in a substantial variance in the total liquid dispense, e.g., about 0.5 to 1.0 microliter, for example. With the trim pump arrangement, which is, of course, optional in the apparatus of the present invention, the pipettor can be easily and readily adjusted to make very small or minute changes in the total volume of liquid dispensed.

The sample pump 107 has a delivery capacity which is sufficient to handle substantially all of the liquid to be dispensed. The second or trim pump 126 has a delivery capacity which is adjustable as shall be described and which is only a fraction of the capacity of the sample pump 107. The trim pump 126 is connected in series between the sample pump 107 and the sample nozzle 19 via flexible tube 104.

Figure 12:
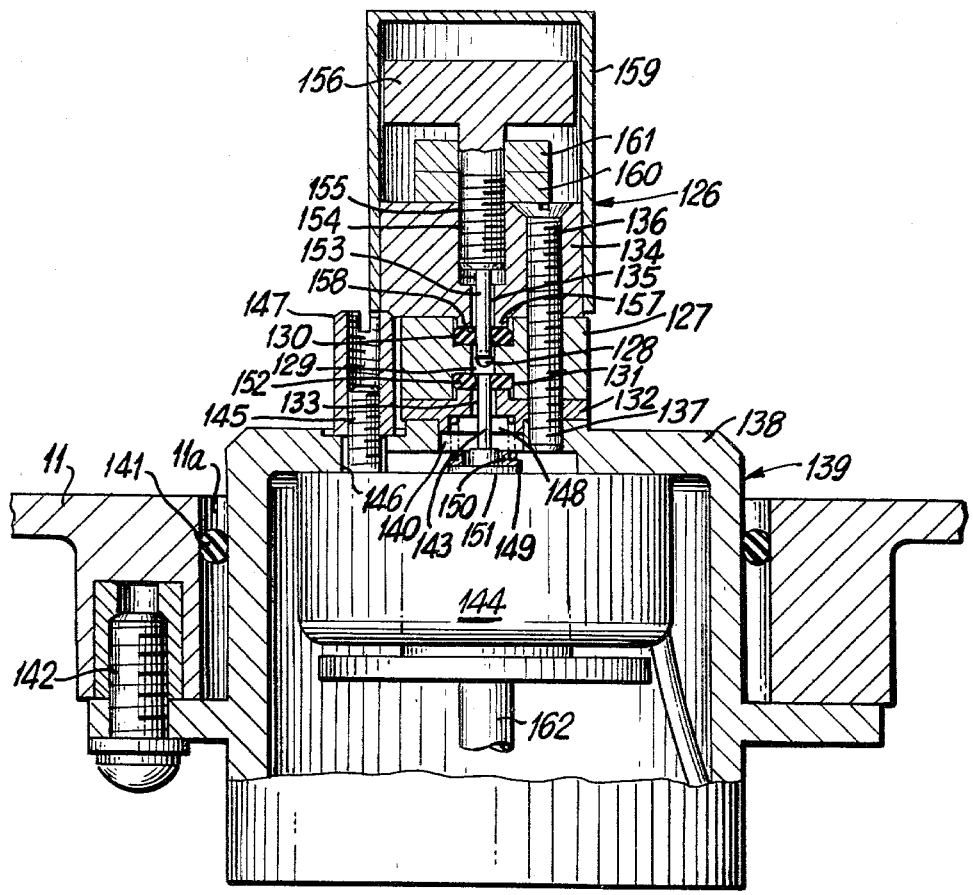
FIG. 12 is an enlarged elevational sectional view of a variable volume trim pump which may be used in conjunction with the sample delivery pump.

The trim pump 126 is shown in greater detail in FIG. 12. As shown, the trim pump comprises a cylindrical valve body 127 having a diametrically disposed, horizontal bore 128 for a passage of the sample liquid. The valve body 127 also includes an axial bore 129 which intersects the horizontal bore 128 and terminates in enlarged diameter recesses 130, 131, respectively, at each opposite end of the valve body 127. A circular base plate 132 having a central opening 133 is mounted against the bottom end of the valve body 127. Similarly, a valve cover plate 134 having a central opening 135 is mounted against the top end of the valve body 127. Both the base plate 132 and the cover plate 134 are held in place with their respective central openings 133, 135 in alignment with the axial bore 129 by means of flat heads screws as at 136. These screws pass through the top cover plate 134, pump body 127 and base plate 132 and threadably engage tapped holes 137 in the top wall 138 of an enlarged bell-shaped heat sink 139. The top wall 138 also has an enlarged central opening 140 which aligns with the opening 133 in base plate 132.

The housing 139 is mounted inside an enlarged diameter opening 11a in the top cover 11 of the pipettor apparatus. A seal ring 141 is disposed in the space between the housing 139 and the side walls of the opening 11a and the whole assembly is secured in place by set screws as shown at 142.

An elongated, small diameter piston 143 passes through the central opening 133 and extends into the axial bore 129 in pump body 127. The elongated piston 143 is driven in either one of two directions in the axial bore 129 by an electrically-activated motor 144. The motor 144 in this instance is preferably a solenoid of conventional design and is secured in place by threaded studs as at 145 which pass through corresponding holes 146 in top wall 138 and by round nuts 147.

A compression spring 148 is mounted inside a circular recess 149 in the bottom of the base plate 132 and is held in place by a spring retainer 150 and retainer ring 151 which is attached to piston 143. The spring 148 bias the piston 143 back against the solenoid body 144 retaining it there when the solenoid 144 is de-energized. An O-ring 152 is placed inside the circular recess 131 and seals off the lower end of the axial bore 129 under the assembly load applied by screws 136 through the base plate 132.

An adjustable pin 153 is mounted inside the central opening 135 of the top cover plate 134 and also extends into the axial bore 129. The pin 153 is attached to the lower end of a screw 154 and is moveable in either direction inside the axial bore 129. The location of the pin 153 can be precisely adjusted by means of the screw 154 which is threaded inside the enlarged diameter opening 155 in the top cover plate 134. A nob 156 is fixedly secured to the screw 154 for convenience in making necessary adjustments in the location of the pin 153.

Top cover plate 134 also includes a circular protuberance 157 which fits inside the circular recess 130 at the top end of the pump body 127. An O-ring 158 is placed inside the circular recess 130 and is held under compression by the protuberance 157 to seal off the upper portion of the axial bore 129.

A transparent plastic cap 159 is provided to cover the knob 156 and prevent any accidental movement once the knob has been adjusted. Suitably the side walls of the plastic cap 159 can be made to fit snuggly over the top cover plate 134 and yet permit the cap to be easily removed when necessary. Also, if desired, a pair of can blocks 160, 161 maybe arranged around the adjustable screw 154 along with a locking pin (not shown) in order to provide a limiting means for making total stoke adjustments for pin 153 and thereby limiting the stoke of piston 143.

As indicated, the solenoid motor 144 is of a conventional design and includes a drive shaft of 162 which is fixedly secured to the lower end of the elongated piston 143. The upward movement of the drive shaft 162 is limited by the pin 153 attached to the knob 156 and screw 154, while the downward movement of the shaft 162 attached to piston 143 is limited by retainer 151 which is attached to piston 143 and acts against the solenoid 144.

In operation of the sample pump 107 (FIG. 11), a series of short electrical pulses are fed from a control circuit as hereinafter described to the stepper motor 112 via the cable 119 to actuate the stepper motor and lower the piston 113 thereby drawing or aspirating a specified amount of sample from one of the sample viles 16 located at the "pick-up" postion B or C as shown in FIG. 1. Typically, the design of the stepper motor 112 maybe such that each pulse causes the rotor to rotate through an angle of 7.5° and the shaft 114 to move a corresponding distance in the linear direction. After the sample arm 17 has been lifted to remove the nozzle 19 from the vile 16 and relocate the nozzle at the fill position, a series of short electrical pulses are again fed to the motor 112 but in this instance the polarity of the stationary poles are reversed and the piston 113 is caused to move via shaft 114 in an upward direction, i.e., compression stroke, expelling the sample through the sample nozzle 19. This procedure is preferably repeated several or more times with the same quantities of liquids to be dispensed. If the amount of liquid actually expelled through the nozzle 19 is consistently below the amount specified or desired, then an appropriate adjustment can be made to the trim pump 126 to compensate for this deficiency. This adjustment is quite easily made by simply rotating the knob 156 on the threaded stem 154 in a counter-clockwise direction which in turn raises the pin 153 to a new location inside the axial bore 129. During the next and subsequent vacuum strokes of the piston 143 in pump 126 to draw liquid through the nozzle 19, the elongated piston 143 is drawn downwardly in axial bore 129 to its stop postion as hereinabove described when the solenoid motor 144 is de-energized. It will be seen that in this mode of operation the elevation of the pin 153 in axial bore 129 will allow a small additional volume of liquid to be drawn through the nozzle 19 into the tube 104 (FIGS. 9 and 10). The stepper motor 112 is again activated by a series short electrical pulses but in this instance the polarity of the stationary poles are again reversed and the shaft 114 moves the piston 113 upwardly in its compressive stroke to expel liquid in the tube 104 through the nozzle 19. This procedure can be repeated again if necessary to readjust the location of the pin 153 in axial bore 129 until the actual amount of liquid expelled through the nozzle 19 concides exactly with the specified amount of liquid to be dispensed.

Conversely, if the amount of liquid actually expelled through the nozzle 19 is greater than the amount specified or desired, then the pump 126 can be adjusted in a similar manner to remove a small amount of liquid from the tube 104. This is readily accomplished by rotating the knob 156 on the threaded stem 154 in a clockwise direction which in turn results in lowering the pin 153 in axial bore 129. The motor 112 of sample pump 107 (FIG. 11) is again actuated by a series of short electrical pulses and the piston 113 is raised in its compressive stroke and thereby expels liquid from the tube 104 through the nozzle 19. At the same time, an electrical signal is fed to the solenoid motor 144 (FIG. 12) which activates the motor and moves the elongated piston 143 upwardly in the axial bore 129 until it contacts the lower end of the pin 153 and comes to rest. The movement of the piston 143 in axial bore 129 causes a small additional amount of liquid to be expelled through the tube 104 and the sample nozzle 19. This procedure can be repeated again until the exact amount of liquid to be dispensed is actually expelled through the nozzle 19. Once the pump 126 has been finally adjusted to either add or subtract the required amount of liquid in the tube 104, no further adjustments are generally necessary so long as the same liquid is dispensed through the same nozzle.

With reference now to FIG. 13 of the drawing, there is shown a block diagram which illustrates the control circuit for operating the various components of the pipettor apparatus. This circuit is incorporated on two circuit boards, a CPU board 164 and a motor driver board 165 (see FIG. 4). As shall be described in detail hereinafter, the CPU board 164 incorporates an 8085 microprocessor and has an RS 232 terminal for connection to an external computer, if desired. The CPU board 164 is also connected to a 120 volt, 60 cycle power supply 166 (see also FIG. 4) having a 12 volt and 5 volt output terminal. The 120 volt terminal is connected to a fan assembly 167 for cooling the various component parts and also to a filter assembly 168. As shown in FIG. 4, the fan 167 is disposed to direct a stream of coolant air against a baffle plate 169 which in turn directs the coolant toward the reagent and sample pumps 105, 106, and 107. A main switch 170 simultaneously activates the power supply 166, fan assembly 167 and filter assembly 168.

The CPU board 164 is also directly connected to the motor driver board 165 via the ribbon cable 171 and also to the LED board 172 via the ribbon cable 173. The LED board operates the various LEDs (not shown)

mounted on the front panel 10a. These LEDs visually display to the operator all test parameters under which the pipettor apparatus is to be operated. The front panel 10a further includes a keyboard panel 174 and a seven segment display 175 which are also connected to the CPU board 164 via the ribbon cable 176. It will be evident therefore that prior to operation of the pipettor apparatus, the operator can select a given program involving a certain number of specific samples to be tested and also the reagents, sample and diluent volumes that are to be employed in the test by simply transferring the information via the keyboard panel to the logic circuits incorporated in the CPU board as shall be described in greater detail hereinafter.

During operation of the pipettor apparatus, the microprocessor and other operating components of the control circuit are responsive to various signals fed to the CPU board from the photosensors via a series of electrical leads 177a through 177h. These leads are connected respectively to the photosensors 101 for the sample arm (vertical), 88 for the reagent arm (vertical), 74 for the lateral arm drive mechanism (hereinafter referred to simply as "lateral arm"), 120 for the sample pump, 36 for the transfer disc, 58 for the sample ring, 178 for the first reagent pump and 179 for the second reagent pump. The signals fed from the photosensors correspond to the position of each of the various components at a particular time in question, i.e., whether or not the component is at the "home" position. These signals are processed through the CPU circuit which includes logics as shall be described and corresponding output signals are fed to the motor driver board 165 via the cable 171. This circuit is connected to the 5 and 12 volt terminals of the power supply 166 via the lead 180 and contains a series of stepper control circuits, there being eight such circuits as depicted at 181a-181h. Each control circuit is then connected in turn to the individual stepper motors for the various components via the power cables in the manner as already described. In the case of the two reagent pumps which were not separately described, the control circuits are connected respectively to the stepper motor 182 for the first reagent pump 105 via the cable 183 and the stepper motor 184 for the second reagent pump 106 via the cable 185. The circuit board 165 also includes separate control circuit for driving the solenoid 144 of the trim pump 126 via the cable 163.

Figure 14:
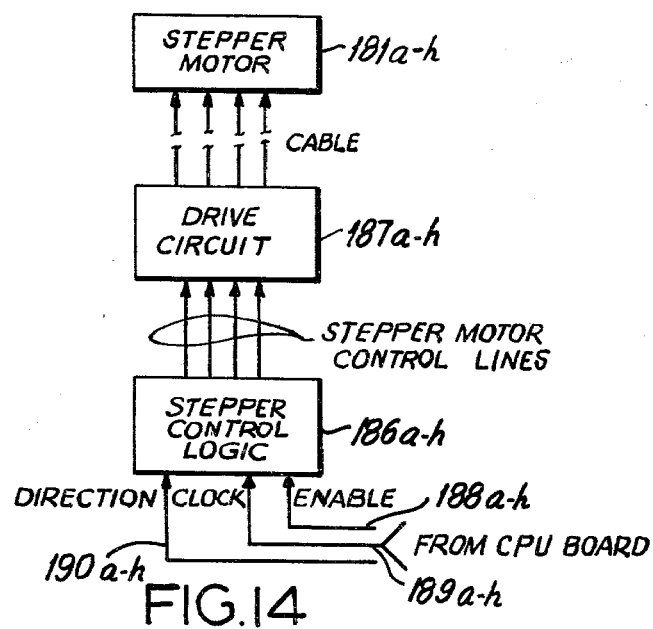
FIG. 14 is a block diagram showing in greater detail the control circuit for each stepper motor on the motor drive board illustrated in FIG. 13.

As shown more particularly in FIG. 14, the stepper control circuits 181a-181h include control logics 186a-186h and separate drive circuits 187a-187h. The control logics 186a-186h are responsive to three separate signals fed from the CPU board 164, i.e., an enable signal via the leads 188a-188h, a series of timed pulses fed from a clock in the CPU circuit via the leads 189a-189h and a separate signal indicative of direction via the leads 190a-190h. These signals are in turn translated into output signals from the logic circuits 186a-186h and are fed to the drive circuits 187a-187h where the signals are amplified and then fed directly to the stepper motors via the respective cables as described hereinabove.

Figure 15:
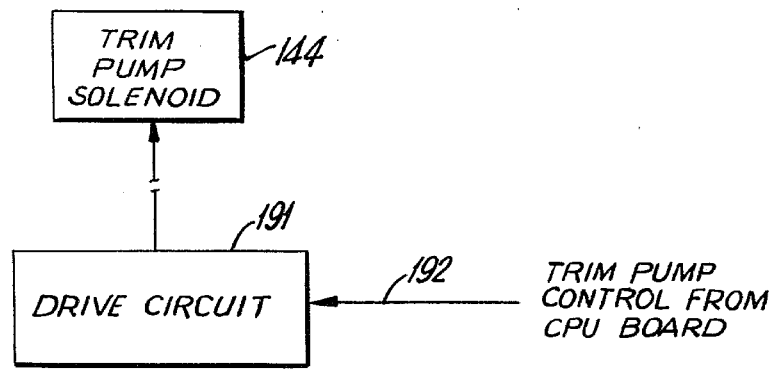
FIG. 15 is a block diagram showing the control circuit for driving the trim pump solenoid motor.

The drive circuit for the trim pump solenoid 144 is shown in FIG. 15. It comprises basically a drive circuit 191 for amplifying the control signal 192 from the CPU board to either energize or de-energize the solenoid.

Figure 16:
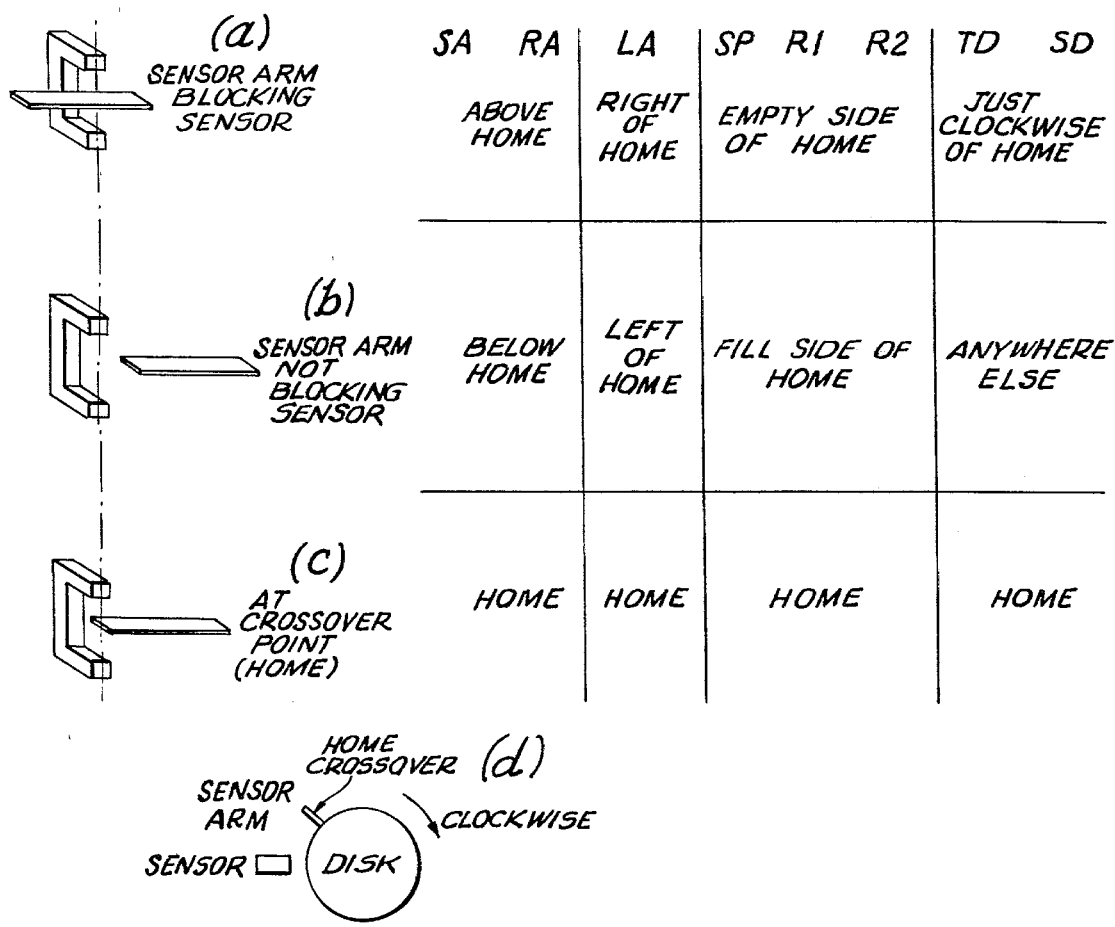
FIGS. 16(a), 16(b), 16(c) and 16(d) are perspective views of the optical sensors used for the various operating components of the pipettor apparatus showing separately the different positions of the sensor element and the corresponding locations of the operating components.

FIG. 16 schematically shows the various positions of the sensor arm with respect to each of the photosensors and the corresponding location for the respective components. For example, in FIG. 16a where the sensor arm completely interrupts or blocks the lightbeam, the sample arm and reagent arm are both above the home position, the lateral arm drive mechanism is to the right of home and the sample pump and two reagent pumps are at the empty side of home. Conversely, as shown in FIG. 16(b) where the sensor arm does not block the light beam, the sample arm and reagent arm are below the home position, the lateral arm drive mechanism is to the left of home and the sample pump and two reagent pumps are at the fill side of home. At the point where the sensor arm first crosses over and just begins to block the light beam as shown in FIG. 16(c), the sample arm and reagent arm are at the home position, the lateral arm mechanism is also at the home position as well as the sample pump and two reagent pumps. FIG. 16(d) shows schematically the equivalent three positions of the transfer disc 12 and sample ring 15. It should be noted in this connection that the disc or ring will rotate only in the clockwise direction when it moves to the home position. Thus, the three possible positions that can be occupied by the sensor arm are (1) at the crossover point or home position where the sensor arm just begins to block the light beam (2) just clockwise of this home position (3) anywhere else. It will be seen therefore that the control circuit in the CPU board can determine at any instance of time the position of each one of the various components of the pipettor apparatus with respect to the home position. It will be further seen that the control circuit is capable of activating any one or a number of the components simultaneously to perform various functions as shall be described in greater detail hereinafter by feeding appropriate signals to the motor drive circuit which in turn operates the individual stepper motors or the solenoid for the trim pump.

Figure 17:
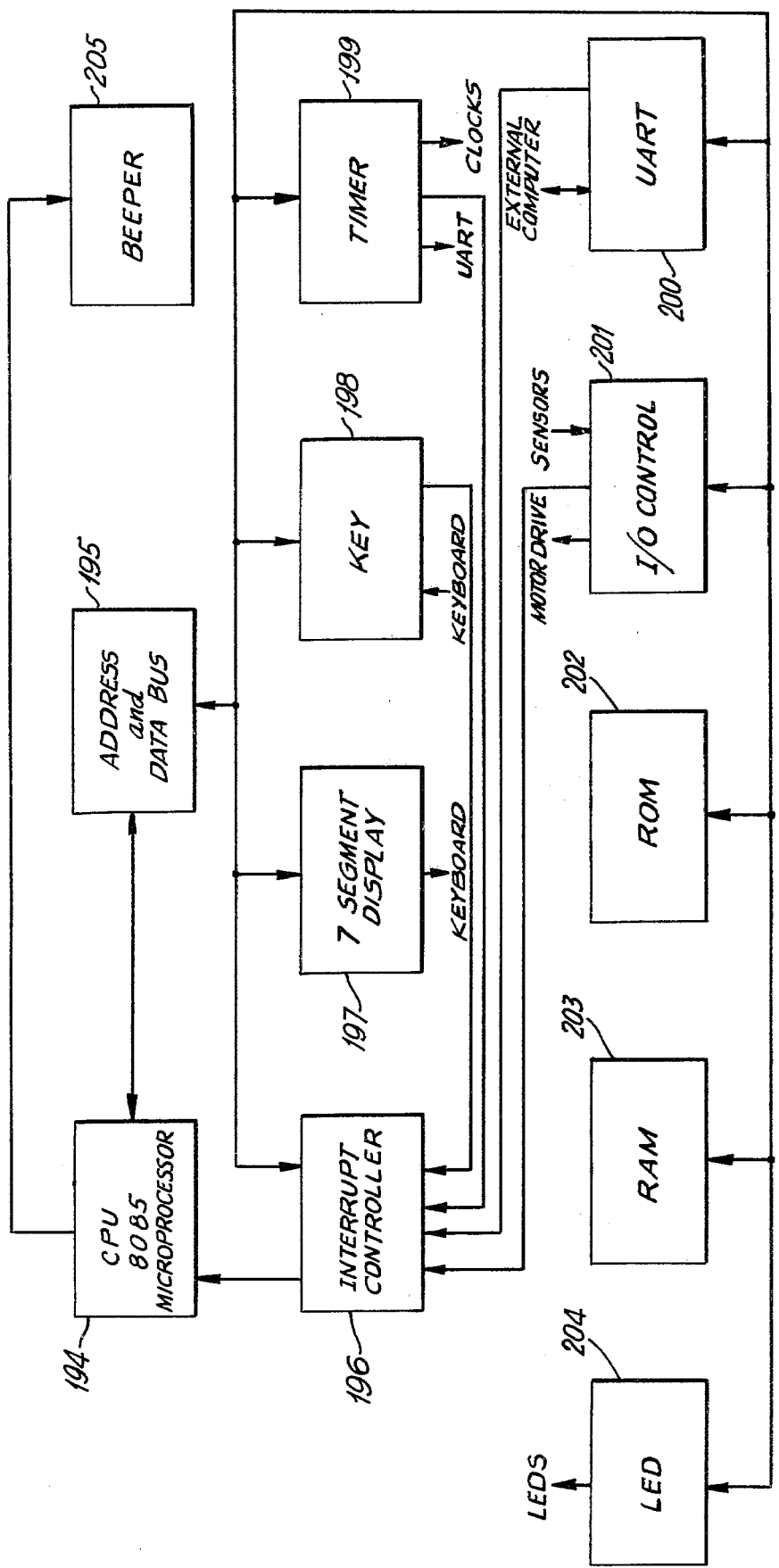
FIG. 17 is a block diagram showing in detail the various components of the CPU board illustrated in FIG. 13.

FIG. 17 shows a block diagram of the various elements which are used in the control circuit on the CPU board. The heart of the control circuit is the 8085 microprocessor 194. The microprocessor communicates bi-directionally with the address and data bus 195 to all peripheral elements and also receives additional signals from an interrupt controller 196. The address and data bus 195 communicates in turn bi-directionally with the interrupt controller 196, seven segment display circuit 197, the keyboard circuit 198, timer 199, UART (Universal Asynchronous Receiver-Transmitter) as at 200, and Input-Output control as at 201, ROM 202, RAM 203 and LED circuit 204. The microprocessor 194 also communicates directly with a beeper circuit 205. The address and data bus 195 functions to control all on-board communications between the microprocessor 194 and the various other elements of the circuit. The control circuit may be connected directly to an external computer by means of the UART 200 if desired. The timer 199 generates four clock signals, three of which drive leads 189a-189h (FIG. 14), and the other which is used by the UART. The program used by the microprocessor 194 is stored in non-volatile memory available in the ROM 202. Additional volatile memory is available in the RAM 203. The microprocessor 194 controls direction leads 190a-190h, enable leads 188a-188h, and monitors the sensors via the Input-Output control 201.

The operation of a pipettor apparatus in accordance with the present invention is best illustrated by the following example:

A typical pipettor program for filling a designated number of cuvets in a transfer disc 12 with sample specimen and reagent is divided essentially into four parts: (1) Initialization, (2) Sample Area, (3) Wrap-Up, and (4) Clean.

In Part (1) "Initialization", Cuvet No. 0 is filled a water blank and Cuvet No. 1 is filled with reagent and a water blank. In Part (2) "Sample Area", designated cuvets are each filled with sample specimen, diluent and reagent ($R_1, R_2$). In Part (3) "Wrap-Up", the remaining cuvets which are not used in the test are filled with water. Finally, in Part (4) "Clean", each of the sample and reagent nozzles 19, 20 and 21 are cleaned with wash water for use in the next test.

In the example, each part of the pipettor program will be described separately along with the various operations performed by the pipettor components, i.e., sample and reagent arms, pumps, transfer disc, etc. As shall be indicated, some of the operations are performed in sequence while others are performed simultaneously or a combination of both. The program to be described is stored in the memory circuits of the CPU board, i.e., in ROM 202 and RAM 203. The parameters of each test, such as diluent and reagent volumes, etc., are "keyed" into the computer via the keyboard 174 on the front panel 10a. All the test parameters are visually displayed by the LEDs 172 also on the front panel 10a.

Figure 18:
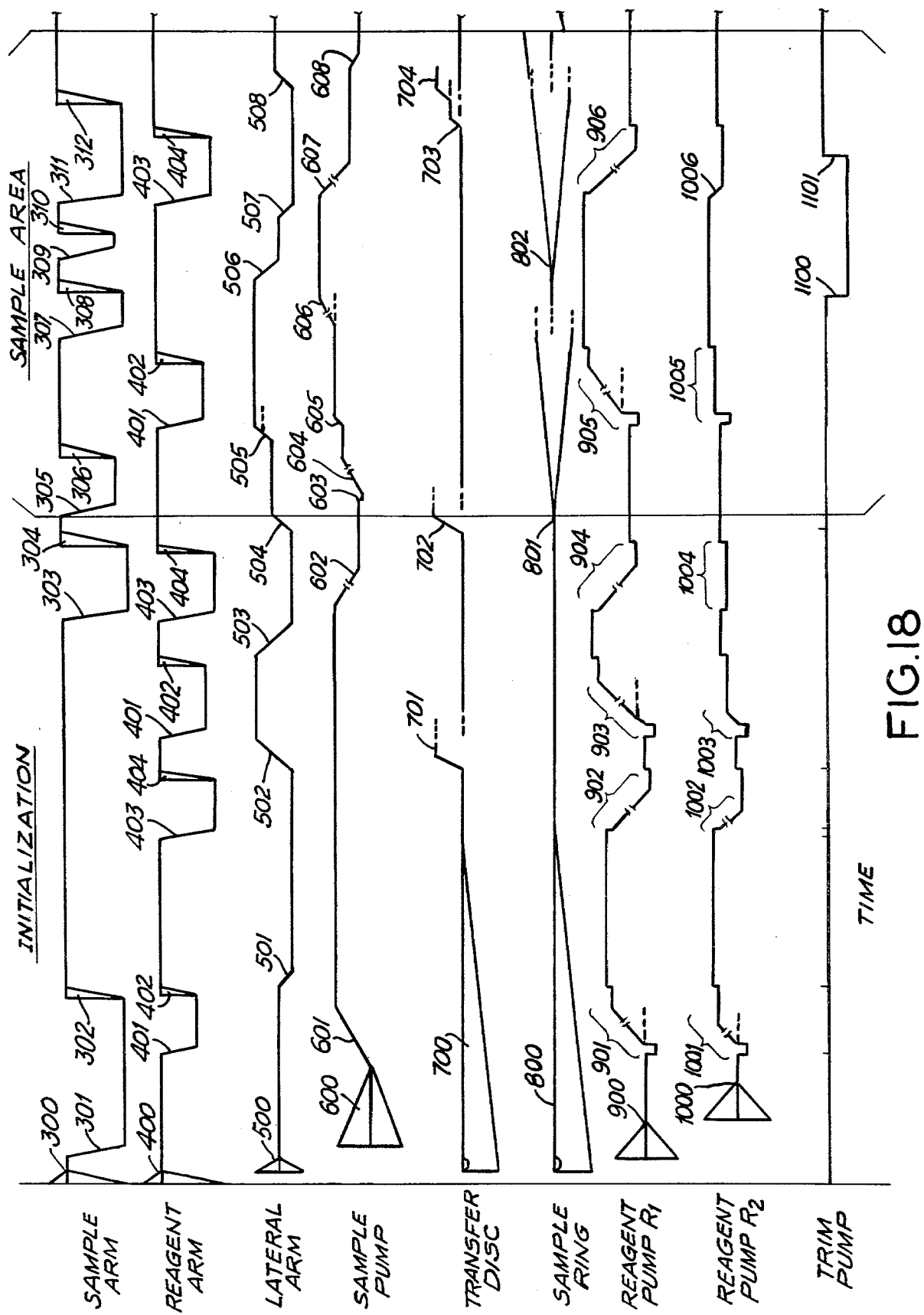
FIG. 18 is a function-time chart illustrating the sequence of operation of the various components of the pipettor apparatus.

Reference numerals used in the description refer to the corresponding operations performed by the pipettor components as shown in the function-time chart of FIG. 18. In the chart, there are shown a total of nine functions performed by the pipettor components: (1) vertical movement of sample arm 17, (2) vertical movement of reagent arm 18, (3) lateral movement of both sample and reagent arms, (4) aspirate and dispense strokes of the sample pump 107, (5) rotation of the transfer disc 12, (6) rotation of the sample ring 15, (7) aspirate and dispense strokes of the first reagent pump 105 ($R_1$), (8) aspiration and dispense strokes of the second reagent pump 106 ($R_2$), and (9) activation of the trim pump 126. The first eight of the above functions are driven by the respective stepper motors 95, 80, 68 etc. (see FIG. 13). The ninth function which is the trim pump is driven by the solenoid 144.

The following terms are used in the description to explain the various operations:

"Home" means to move the device to its home position according to the homing routine described hereinabove (see FIG. 16).

"Move" means to start the device toward its destination and wait for its arrival.

"Send" means to start the device toward its destination but do not wait for its arrival.

"Wait" means to pause until a specified device has reached its destination.

"$R_1$ Vol." means reagent 1 volume selected for this test.

"$R_2$ Vol." means reagent 2 volume selected for this test.

"Diluent Vol." means diluent volume selected for this test.

"Sample Vol." means sample volume selected for this test.

PART 1—INITIALIZATION

Initialization of the pipettor program is attained by the following operations:

(I) Simultaneously home (a) sample arm (300) and (b) reagent arm (400).

(II) Send sample ring home (800).

(III) Send transfer disk home (700).

(IV) Home lateral arm (500).

(V) This operation is divided into two groups which are performed simultaneously. The first group comprises the following steps:

(a) Move sample arm down into water (301);
(b) Move sample pump (600);
(c) Sample pump aspirates 225 microliters water (601);

The second group of steps which are performed simultaneously with (a), (b), and (c) comprises:

(d) Home reagent pump $R_1$ (900);
(e) Home reagent pump $R_2$ (1000);
(f) Reagent Pick-Up Routine—Reagent pump $R_1$ aspirates $R_1$ Vol. plus Diluent Vol. (901) while simultaneously reagent pump $R_2$ aspirates $R_2$ Vol. (1001). This operation shall be described in greater detail hereinafter.

The second group of steps which are performed simultaneously with (a), (b) and (c) comprises:

(d) Move sample arm down into water (301);
(e) Home sample pump (600);
(f) Sample pump aspirates 255 microliters water (601);
(g) Home sample arm (302).

In the case of viscous reagents (such as bilirubin), steps (d) (e) and (f) shown above are skipped. After (g), the Lateral Arm moves to C,C' and then (d) (e) and (f) are performed.

(VI) Move lateral arm to position sample nozzle 19 and reagent nozzles 20, 21 at A and A' (501). At this point, the sample and reagent nozzles are positioned directly over Cuvet No. 0 in the transfer disc.

(VII) Reagent Dispense Routine—Reagent pump $R_1$ dispenses $R_1$ Vol. plus Diluent Vol. (902) while simultaneously reagent pump $R_2$ dispenses $R_2$ Vol. (1002). This operation shall also be described in greater detail hereinafter.

(VIII) Send transfer disc to Cuvet No. 1 (701).

(IX) Move lateral arm to position sample nozzle 19 and reagent nozzles 20, 21 at B and B' or C and C', respectively (502). At this point, the sample nozzle is directly over one of the sample vials 16 in the sample ring 15 and the reagent nozzles 20, 21 are directly over the compartments 14a and 14b, respectively, of the reagent container 14.

(X) Reagent Fill Routine—Reagent pump $R_1$ aspirates $R_1$ Vol. plus a carry along volume (903) while simultaneously reagent pump $R_2$ aspirates a carry along volume (1003).

(XI) Move lateral arm to position the sample nozzle 19 and reagent nozzles 20, 21 at A and A' (503). At this point, the sample nozzle and reagent nozzles are directly over Cuvet No. 1.

(XII) This operation is divided into two groups which are performed simultaneously. The first group comprises a reagent dispense routine in which reagent pump $R_1$ dispenses $R_1$ Vol. (904), while simultaneously reagent pump $R_2$ dispenses 0 volume (1004).

The second group of steps which are performed in simultaneously comprises:

(a) Lower sample arm into the transfer disc (303).
(b) Sample pump dispenses Diluent and Sample Vol. (602).

(XIII) Home sample arm (304).

(XIV) Send transfer disc to Cuvet No. 2 (702).

(XV) Send sample ring to locate first sample vial at pick-up position B or C (801).

(XVI) Move lateral arm to position the sample nozzle 19 and reagent nozzles 20, 21 at D and D' in FIG. 1 (504). At this point, the sample nozzle and reagent nozzles are directly over the larger compartment 22a of the wash container 22.

This concludes Part 1—Initialization of the pipettor program.

PART 2—SAMPLE AREA

In this part of the pipettor program, the designated cuvets in the transfer disc are filled with sample solution, diluent and reagent. The program operations are as follows:

(I) Sample arm is lowered into wash water (305).

(II) Sample pump dispenses 6 microliters of air (603).

(III) Sample pump aspirates Diluent Vol. plus purge volume plus 6 microliters of water (604).

(IV) Home sample arm (306).

(V) Move lateral arm to position the sample nozzle 19 and reagent nozzles 20, 21 at B and B' or at C and C', respectively, (505).

(VI) This operation includes both a reagent and sample fill routine. Both routines are performed simultaneously in two separate groups of steps. In the first group, the reagent pick-up routine, reagent pump $R_1$ aspirates $R_1$ Vol. (905) while, simultaneously, the reagent pump $R_2$ aspirates $R_2$ Vol. (1005).

The second group of steps, i.e., the sample fill routine, are performed as follows:

(a) Sample pump aspirates 2 microliters of air (605). This step is performed to incorporate a small volume of air which separates the diluent from the sample solution.

(b) Lower sample arm into sample vial (307).

(c) Sample pump aspirates Sample Vol. (606) plus 2 additional microliters (not shown). This step is carried out very slowly for purposes of accuracy.

(d) Sample pump dispenses 2 microliters (not shown).

(e) Trim pump is activated (1100).

(f) Home sample arm (308).

(VII) Send sample ring to index next sample vial 16 at fill position (802).

(VIII) Move lateral arm to position the sample nozzle 19 and the reagent nozzles 20, 21 at H and H', respectvely, in FIG. 1 (506). At this point, the sample nozzle is located directly over the smaller compartment 22b of the wash container 22 and the reagent nozzles 20, 21 are located directly over the larger compartment 22a.

(IX) Sample arm is lowered into wash water (309).

(X) Home sample arm (310). This step in combination with (IX) serves to clean the outside surfaces of the nozzle tip.

(XI) Move lateral arm to position the sample nozzle 19 and reagent nozzles 20, 21 at A and A', respectively, (507).

(XII) This operation is a reagent dispense routine. It may involve (1) reagent $R_1$ Vol. alone or (2) both reagent $R_1$ Vol. and reagent $R_2$ Vol. In the case where $R_1$ Vol. and $R_2$ Vols. are used, the reagents are dispensed into the cuvet (906 and 1006) and the next operations XIII, XIV and XV, as hereinafter described, are performed in sequence. However, in the case where $R_1$ Vol. alone is used, then $R_1$ Vol. (906) is dispensed into the cuvet while the next operations indicated above are performed simultaneously.

(XIII) Sample arm is lowered into cuvet (311).

(XIV) Sample pump dispenses Diluent Vol. plus 2 microliters of air plus Sample Vol. (607).

(XV) Activate trim pump (1101).

(XVI) Move transfer disc so that sample nozzle contacts sidewall of cuvet for sidewipe (703).

(XVII) Home sample arm (312). This step includes sidewipe which removes any drops that cling to the nozzle tip.

(XVIII) Send transfer disc to next cuvet (704).

(XIX) Move lateral arm to postion sample nozzle 19 and reagent nozzles 20, 21 at H and H', respectively (508).

(XX) Sample pump dispenses purge volume (608).

Repeat operations (I)-(XX) until all of the designated cuvets are filled.

PART 3—WRAP-UP

Each of the remaining cuvets (not designated in test) are filled with water in the following operations:

(I) Move lateral arm to position sample nozzle 19 and reagent nozzle 20, 21 at C and C', respectively (509).

(II) Reagent arm is lowered to just above reagent container (405).

(III) Simultaneously move (a) reagent pump $R_2$ to home (907), and (b) reagent pump $R_2$ to home (1007).

(IV) Home reagent arm (406).

(V) Move lateral arm to position sample nozzle 19 and reagent nozzles 20, 21 at H and H', respectively (510). In case of viscous reagents move Lateral Arm to C, C' not H, H'.

(VI) This is a reagent pick-up routine. Simultaneously (a) reagent pump $R_1$ aspirates $R_1$ Vol. plus Diluent Vol. (908), and (b) reagent pump $R_2$ aspirates $R_2$ Vol. (1008).

(VII) Move lateral arm to position sample nozzle 19 and reagent nozzles 20, 21 at A and A', respectively (511).

(VIII) This is a reagent dispense routine. Simultaneously (a) reagent pump $R_1$ dispenses $R_1$ Vol. plus Diluent Vol. (909), and (b) reagent pump $R_2$ dispenses $R_2$ Vol. (1009).

(IX) Send transfer disc to next cuvet (705).

All of the above operations (I)-(IX) are repeated until all of the remaining cuvets are filled.

PART 4—CLEAN-UP

The following operations are performed in order to clean the sample and reagent nozzles for use in the next batch of tests.

These operations begin after the transfer disc moves to the next cuvet and the sample ring indexes the sample volume.

(I) Move lateral arm to position sample nozzle 19 and reagent nozzles 20, 21 at D and D', respectively (512). At this point, the sample nozzle and reagent nozzles are both directly over the larger compartment 22a of the wash container 22.

(II) Move sample arm down into water (313).

(III) Home sample pump (609).

(IV) Home sample arm (314).

(V) Simultaneously (a) reagent pump $R_1$ aspirates 40 microliters of water (910) and (b) reagent pump $R_2$ aspirates 20 microliters of water (1010).

(VI) Home reagent pump $R_1$ (911).

(VII) Home reagent pump $R_2$ (1011).

(VIII) Move lateral arm to home position H and H' (513).

(IX) Reagent arm is lowered to just above wash container (407).

(X) Home reagent pump $R_1$ (912).

(XI) Home reagent pump $R_2$ (1012).

(XII) Lower reagent arm into wash container (408).

(XIII) This is a reagent pick-up routine. Simultaneously (a) reagent pump $R_1$ aspirates $R_1$ wash volume (913), and (b) reagent pump $R_2$ aspirates $R_2$ wash volume (1013).

(XIV) This is a reagent dispense routine. Simultaneously (a) reagent pump $R_1$ dspenses $R_1$ wash volume (914), and (b) reagent pump $R_2$ dispenses $R_2$ wash volume (1014).

Steps (XIII) and (XIV) are repeated three times.

(XV) Home reagent arm (409).

(XVI) Move lateral arm to position the sample nozzle 19 and reagent nozzles 20, 21 at R and R', respectively (514).

The aforegoing description outlines the operation of the pipettor apparatus except for the reagent fill and empty routines which were only briefly described. These routines will now be described in greater detail.

REAGENT PICK-UP ROUTINE

Figure 18A:
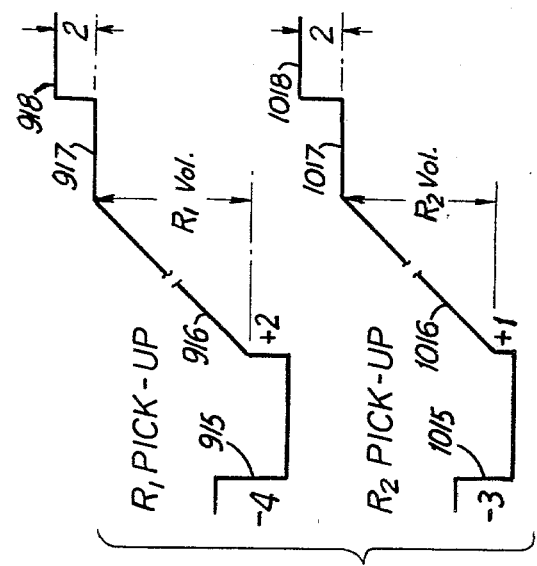
FIG. 18A is an enlarged view of a portion of the chart in FIG. 18 showing the reagent pick-up routine in greater detail.
Figure 18B:
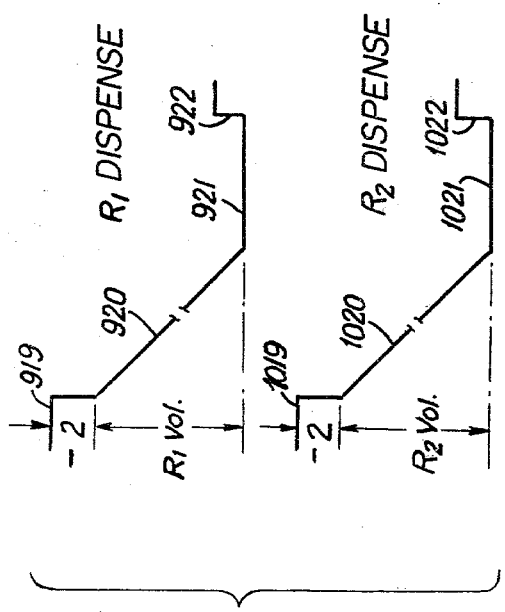
FIG. 18B is a similar view showing the reagent dispense routine in greater detail.
Figure 18:
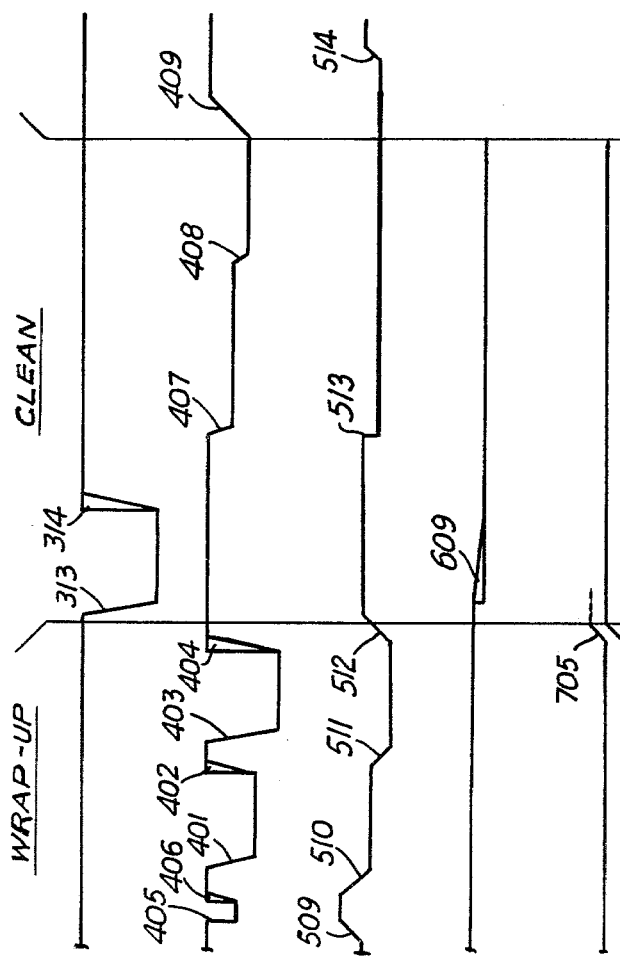

The reagent pick-up routine is shown in greater detail in FIG. 18A. It comprises the following operations:

(I) Simultaneously (a) reagent pump $R_1$ expels 4 microliters of air (915) and reagent pump $R_2$ expels 3 microliters of air (1012).

(II) Move reagent arm down into reagent container (401).

(III) Simultaneously (a) reagent pump $R_1$ aspirates $R_1$ Vol. plus 2 microliters of fluid (916), and (b) reagent pump $R_2$ aspirates $R_2$ Vol. plus 1 microliter of fluid (1016).

(IV) Pause one second if reagent solution is viscous such as in the case of Bilirubin reagent (917 and 1017). This pause allows extra time for the fluid pressure in the nozzle tip to reach an equilibrium condition before any movement of the reagent arm.

(V) Home reagent arm (402). In the case of viscous reagents, home reagent arm slowly.

(VI) Simultaneously (a) reagent pump $R_1$ aspirates 2 microliters of air (918), and (b) reagent pump $R_2$ aspirates 2 microliters of air (1018).

This concludes the reagent pick-up routine.

REAGENT DIPSENSE ROUTINE

The reagent dispense routine comprises the following steps:

(I) Move reagent arm down into cuvet area (403).

(II) Simultaneously (a) reagent pump $R_1$ expels 2 microliters of air (919), and (b) reagent pump $R_2$ expels 2 microliters of air (1019).

(III) Simultaneously (a) reagent pump $R_1$ dispenses $R_1$ Vol. (920), and (b) reagent pump $R_2$ dispenses $R_2$ Vol. (1020).

(IV) Pause one second before movement of reagent arm if reagent is viscous solution (921 and 1021).

(V) Home reagent arm (404).

(VI) Simultaneously (a) reagent pump $R_1$ aspirates 2 microliters of air (922), and (b) reagent pump $R_2$ aspirates 2 microliters of air (1022).

This concludes the reagent dispense routine.

It will be understood from the foregoing description that many changes and modifications may be made in the pipettor apparatus and its operation without departing from the spirit and scope of the present invention. As indicated, for example, the pipettor apparatus may be operated successfully with the sample pump alone, i.e., without the trim pump in combination. Other such modifications will readily occur to those skilled in the art.

What is claimed is:

1. Apparatus for automatically and rapidly transferring accurate and precise multiple quantities of sample and reagent solutions from receptacles to a rotatable transfer disc adapted for use in a centrifugal analyzer, said transfer disc having a plurality of radial cavities therein which are divided into separate sample and reagent sections, said apparatus comprising, in combination:

(a) a case having a top wall;

(b) a rotatable support member for holding said transfer disc at first location on said top wall and for rotating said transfer disc about its central axis;

(c) a rotatable sample holder having a plurality of receptacles therein for holding liquid samples to be analyzed at a second location on said top wall remote from said first location;

(d) means for holding at least one reagent container having a liquid reagent solution therein at a third location on said top wall;

(e) a first transfer arm having a sample nozzle affixed to one end thereof;

(f) a second transfer arm having at least one reagent nozzle affixed to one end thereof;

(g) means for rotatably mounting said first transfer arm at a location on said top wall which is intermediate said first and second locations whereby said first transfer arm having said sample nozzle affixed thereto is able to move laterally in a plane substantially parallel to said top wall and to travel the distance between said sample holder and transfer disc;

(h) means for rotatably mounting said second transfer arm at a location on said top wall which is intermediate said first and third locations whereby said second transfer arm having said reagent nozzle affixed thereto is able to move laterally in a plane substantially parallel to said top wall and to travel the distance between said reagent container and said transfer disc;

(i) a first drive mechanism for rotating said support member so as to selectively index each radial cavity in said transfer disc at a predetermined dispense position.

(j) a second drive mechanism for rotating said sample holder so as to selectively index each sample receptacle at a predetermined sample pick-up position;

(k) a third drive mechanism for laterally moving said first transfer arm and said second transfer arm so as to selectively position said sample nozzle at said sample pick-up or dispense position and said reagent nozzle at said reagent pick-up or dispense position, respectively.

(l) means for pivotally mounting said first transfer arm at said intermediate location so that said first transfer arm is able to move in a plane substantially perpendicular to said top wall to place said sample nozzle into a predetermined sample receptacle when said sample holder is rotated to index said sample receptacle at said sample pick-up position and to place said sample nozzle into the sample section of a predetermined radial cavity when said transfer disc is rotated to index said radial cavity at said dispense position.

(m) means for pivotally mounting said second transfer arm at said intermediate location so that said second transfer arm is able to move in a plane substantially perpendicular to said top wall to place said reagent nozzle into said reagent container at said reagent pick-up position and to place said reagent nozzle into the reagent section of a predetermined radial cavity when said transfer disc is rotated to index said radial cavity at said dispense position;

(n) a fourth drive mechanism for pivotally moving said first transfer arm;

(o) a fifth drive mechanism for pivotally moving said second transfer arm;

(p) a first pump operably connected to said sample nozzle for aspirating a predetermined, accurate and precise quantity of liquid sample when said sample nozzle is placed into said predetermined sample receptacle and for dispensing said liquid sample when said sample nozzle is placed into the sample section of said predetermined radial cavity in said transfer disc;

(q) a second pump operably connected to said reagent nozzle for aspirating a predetermined, accurate and precise quantity of liquid reagent when said reagent nozzle is placed into said reagent container and for dispensing said liquid reagent when said reagent nozzle is placed into the reagent section of said predetermind radial cavity in said transfer disc;

(r) electric motors for driving said first through fifth drive mechanisms, inclusive, and said first and second pumps;

(s) sensor devices for monitoring the relative position of said rotatable support member and said sample holder, the lateral and pivotal position of said first and second transfer arm and the relative position of said first and second pumps and for producing output signals corresponding thereto; and (t) a control circuit including memory means for storing a plurality of instructions for operating said apparatus and for producing a corresponding plurality of output signals and a processor adapted to receive said memory signals and said sensor signals and to produce a plurality of output signals which are selectively fed to each one of said electric motors to effect rotation of said transfer disc and sample holder, lateral and pivotal movement of said first and second transfer arms and activation of said first and second pumps according to said plurality of instructions whereby accurate and precise quantities of sample and reagent solutions are transferred to said plurality of radial cavities in said transfer disc.

2. Apparatus in accordance with claim 1 wherein said rotatable sample holder and said means for holding said reagent container are concentrically located on said top wall.

3. Apparatus in accordance with claim 2 wherein said means for holding said reagent container is a rotatable circular tray.

4. Apparatus in accordance with claim 3 wherein said circular tray has a plurality of circumferentially arranged pockets for holding a plurality of said reagent containers.

5. Apparatus in accordance with claim 3 wherein said rotatable sample holder is a ring mounted concentrically around the circumference of said circular tray.

6. Apparatus in accordance with claim 5 wherein said sample ring includes a plurality of apertures arranged in at least one circular row for holding a plurality of sample vials.

7. Apparatus in accordance with claim 6 wherein the plurality of apertures are arranged in two separate rows for holding a plurality of sample vials.

8. Apparatus in accordance with claim 5 wherein said third drive mechanism includes means for laterally moving said first and second transfer arms in unison between said concentrically located reagent tray and sample ring and said transfer disk.

9. Apparatus in accordance with claim 8 wherein said second transfer arm has a first and second reagent nozzle affixed to one end thereof.

10. Apparatus in accordance with claim 9 wherein said reagent containers are divided into two separate compartments for holding two reagent solutions.

11. Apparatus in accordance with claim 5 further including a container for holding wash solution for cleaning said reagent nozzle.

12. Apparatus in accordance with claim 11 wherein said wash container is mounted on said top wall between said transfer disc and said sample ring.

13. Apparatus in accordance with claim 8 wherein all of said electric motors are stepper motors.

14. Apparatus in accordance with claim 13 wherein said sensor devices are optical sensors.

15. Apparatus in according with claim 8 further including a trim pump operably connected in series between said first pump and said sample nozzle, said trim pump having a delivery capacity which is adjustable and only a fraction of the capacity of said first pump whereby very small changes can be made in the total volume of liquid sample dispensed.

16. Apparatus in accordance with claim 15 wherein said trim pump is driven by an electric solenoid.

17. Apparatus in accordance with claim 13 wherein said first drive mechanism for rotating said support member comprises a housing, a driving shaft rotatably mounted in said housing, said drive shaft having said support member affixed thereto at one end, a pinion gear driven by one of said stepper motors and engaging a larger diameter gear affixed to the opposite end of said drive shaft, the gear ratio between said pinion and larger diameter gears being chosen such that a given number of electrical pulses fed to said stepper motor will rotate said support member through a predetermined angular displacement which indexes each one of said radial cavities in said transfer disc at said dispense position.

18. Apparatus in accordance with claim 17 wherein a sensor arm is affixed to said drive shaft and is adapted to activate said sensor device when a predetermined radial cavity in said transfer disc is indexed at said dispense position.

19. Apparatus in accordance with claim 13 wherein said second drive mechanism for rotating said sample holder comprises a housing, a drive shaft rotatably mounted in said housing, a circular support plate affixed to one end of said drive shaft and including means for removably supporting said sample ring around the outer circumference thereof, a pinion gear driven by another one of said stepper motors and engaging a larger diameter gear affixed to the opposite end of said drive shaft, the gear ratio between said pinion gear and said larger diameter gear being such that a given number of electrical pulses fed to said stepper motor will rotate said sample ring through a predetermined angular displacement which indexes one of said sample receptacles in said sample ring at said pick-up position.

20. Apparatus in accordance with claim 19 wherein a sensor arm is affixed to said drive shaft and is adapted to activate said sensor device when a predetermined sample receptacle is indexed at said sample pick-up position.

21. Apparatus in accordance with claim 20 wherein an inner shaft is coaxially and rotatably mounted in said drive shaft and wherein said circular reagent tray is affixed to one end of said inner shaft.

22. Apparatus in accordance with claim 13 wherein said third drive mechanism for laterally rotating said first and second transfer arms comprises a housing, a first and second drive shaft rotatably mounted in said housing, said first and second drive shafts having said first and second transfer arms respectively affixed to one of the ends thereof, a pinion gear driven by another one of said stepper motors and engaging both of a pair of larger diameter gears affixed to the opposite ends of said first and second drive shafts, the gear ratio between said pinion gear and said pair of larger diameter gears being such that a given number of electrical pulses fed to said stepper motor will rotate said first and second transfer arms in unison between said sample ring, reagent container and said transfer disc.

23. Apparatus in accordance with claim 22 wherein a sensor arm is affixed to at least one of said first or second drive shafts and is adapted to actuate said sensor device when said first and second transfer arms are located at a predetermined position intermediate said sample ring, reagent container and said transfer disc.

24. Method for automatically and rapidly transferring accurate and precise multiple quantities of sample and reagent solution to a rotatable transfer disc having a plurality of radial cavities therein, which method comprises;
 (a) placing said transfer disc onto a rotatable support member;
 (b) randomly loading a predetermined number of receptacles containing sample solution into a rotatable sample ring;
 (c) randomly loading a predetermined number of receptables containing reagent solution into a rotatable reagent
 (d) providing a first transfer arm having a sample nozzle at one end thereof adapted to move laterally between said transfer disc and said sample ring and to pivot about a point located near the opposite end thereof whereby said sample nozzle is able to selectively move into a predetermined sample receptable for picking up a specific sample solution;
 (e) providing a second transfer arm having a reagent nozzle at one end thereof adapted to move laterally between said transfer disc and said reagent tray and to pivot about a point located near its opposite end whereby said reagent nozzle is able to selectively move into a predetermined reagent receptable for picking up a specific reagent solution;
 (f) providing a receptacle containing diluent-wash solution at a location intermediate said transfer disc and said sample ring and accessible to said sample and reagent nozzles;
 (g) rotating said transfer disc to index a specific radial cavity to be filled at a designated dispense position;
 (h) rotating said sample ring to index a specific sample receptacle containing a sample solution to be transferred to said transfer disc at a designated sample pick up position;
 (i) rotating said reagent tray to index a specific reagent receptacle containing reagent solution to be transferred to said transfer disc at a designated reagent pick up position;
 (j) laterally moving said first transfer arm and said second arm to locate said sample nozzle and said reagent nozzle at said sample and reagent pick up positions, respectively;
 (k) lowering said sample nozzle into said sample receptacle and aspirating a predetermined, accurate and precise quantity of sample solution therefrom;
 (l) lowering said reagent nozzle into said reagent receptacle and aspirating a predetermined, accurate and precise quantity of reagents solution therefrom;
 (m) laterally moving said first and second transfer arms to said predetermined radial cavity in said transfer disc at said dispense position;
 (n) moving said sample nozzle and said reagent nozzle into said predetermined radial cavity and dispensing said predetermined quantity of sample and reagent solution therein;
 (o) Repeating steps (g) to (n) inclusive until the designated number of radial cavities in said transfer disc are filled with multiple quantities of sample and reagent solution.

25. Method in accordance with claim 24 wherein said predetermined quantity of reagent solution is aspirated and dispensed at a slow rate in the case of viscous liquids and wherein said reagent nozzle is withdrawn also at a slow rate from said reagent solution.

* * * * *